United States Patent
Watanabe et al.

(10) Patent No.: US 11,090,018 B2
(45) Date of Patent: Aug. 17, 2021

(54) RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventors: Minoru Watanabe, Yokohama (JP); Kentaro Fujiyoshi, Tokyo (JP); Sho Sato, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 85 days.

(21) Appl. No.: 16/571,642

(22) Filed: Sep. 16, 2019

(65) Prior Publication Data
US 2020/0008766 A1    Jan. 9, 2020

Related U.S. Application Data

(63) Continuation of application No. PCT/JP2018/005055, filed on Feb. 14, 2018.

(30) Foreign Application Priority Data

Apr. 5, 2017    (JP) .............................. JP2017-075447

(51) Int. Cl.
*G01T 1/17*    (2006.01)
*A61B 6/00*    (2006.01)
(Continued)

(52) U.S. Cl.
CPC .......... *A61B 6/5205* (2013.01); *A61B 6/5258* (2013.01); *A61B 6/54* (2013.01); *H04N 5/32* (2013.01); *H04N 5/361* (2013.01)

(58) Field of Classification Search
CPC ..... A61B 6/4233; A61B 6/542; A61B 6/5205; A61B 6/5258; A61B 6/54;
(Continued)

(56) References Cited

U.S. PATENT DOCUMENTS 7,465,933 B2    12/2008    Ishii et al.
7,541,617 B2    6/2009    Mochizuki et al.
(Continued)

FOREIGN PATENT DOCUMENTS

CN    101849834 A    10/2010
CN    102141630 A    8/2011
(Continued)

OTHER PUBLICATIONS

U.S. Appl. No. 16/103,150, filed Aug. 14, 2018, Atsushi Iwashita.
(Continued)

*Primary Examiner* — Don K Wong
(74) *Attorney, Agent, or Firm* — Venable LLP

(57) ABSTRACT

A radiation imaging apparatus is provided. The apparatus comprises: an imaging region in which a plurality of conversion elements are arranged, wherein the plurality of conversion elements includes a first conversion element configured to obtain a radiation image and a second conversion element configured to obtain irradiation information of incident radiation during radiation irradiation; a storage unit configured to store correction data for correcting a signal output from the first conversion element; and a control unit. The control unit determines a period to cause the first conversion element to perform an accumulation operation in accordance with the irradiation information, determines a correction amount corresponding to the period based on the correction data, and generates a radiation image
(Continued)

signal by correcting a signal output from the first conversion element in accordance with the correction amount after the radiation irradiation.

14 Claims, 18 Drawing Sheets

(51) Int. Cl.
*H04N 5/32* (2006.01)
*H04N 5/361* (2011.01)

(58) Field of Classification Search
CPC ......... H01L 27/14605; H01L 27/14663; H01L 27/14609; H04N 5/32; H04N 5/361; G01T 1/171; G01T 1/20; G01T 1/00; G01T 1/2018; G01T 1/1603; G01T 1/08; G01T 1/026; G01T 1/1663; G06T 11/005; G06T 11/003; G06T 11/00; G06T 7/00; G06T 2201/00; G06T 2200/00
See application file for complete search history.

(56) References Cited

U.S. PATENT DOCUMENTS

| | | | |
|---|---|---|---|
| 7,629,564 B2 | 12/2009 | Mochizuki et al. |
| 7,645,976 B2 | 1/2010 | Watanabe et al. |
| 7,750,422 B2 | 7/2010 | Watanabe et al. |
| 7,812,313 B2 | 10/2010 | Mochizuki et al. |
| 7,812,317 B2 | 10/2010 | Watanabe et al. |
| 7,858,947 B2 | 12/2010 | Mochizuki et al. |
| 7,923,695 B2 | 4/2011 | Ishii et al. |
| 7,932,946 B2 | 4/2011 | Ishii et al. |
| 8,067,743 B2 | 11/2011 | Ishii et al. |
| 8,084,745 B2 | 12/2011 | Mochizuki et al. |
| 8,154,641 B2 | 4/2012 | Nomura et al. |
| 8,368,027 B2 | 2/2013 | Ishii et al. |
| 8,513,611 B2 | 8/2013 | Okada |
| 8,519,344 B2 | 8/2013 | Ishii et al. |
| 8,536,534 B2 | 9/2013 | Okada |
| 8,680,472 B2 | 3/2014 | Mochizuki et al. |
| 8,829,438 B2 | 9/2014 | Sato et al. |
| 8,878,972 B2 | 11/2014 | Wayama et al. |
| 8,981,304 B2 | 3/2015 | Okada |
| 9,048,154 B2 | 6/2015 | Takenaka et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,270,903 B2 | 2/2016 | Wayama et al. |
| 9,277,896 B2 | 3/2016 | Ofuji et al. |
| 9,423,512 B2 | 8/2016 | Sato et al. |
| 9,423,513 B2 | 8/2016 | Watanabe et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,521,347 B2 | 12/2016 | Kawanabe et al. |
| 9,541,653 B2 | 1/2017 | Iwashita et al. |
| 9,625,585 B1 | 4/2017 | Yokoyama et al. |
| 9,661,240 B2 | 5/2017 | Fujiyoshi et al. |
| 9,675,307 B2 | 6/2017 | Ofuji et al. |
| 9,726,767 B2 | 8/2017 | Kawanabe et al. |
| 9,812,474 B2 | 11/2017 | Yagi et al. |
| 9,835,732 B2 | 12/2017 | Fujiyoshi et al. |
| 9,838,638 B2 | 12/2017 | Furumoto et al. |
| 9,948,871 B2 | 4/2018 | Wayama et al. |
| 9,977,135 B2 | 5/2018 | Yokoyama et al. |
| 10,009,990 B2 | 6/2018 | Takenaka et al. |
| 10,068,943 B2 | 9/2018 | Fujiyoshi et al. |
| 10,197,684 B2 | 2/2019 | Terui et al. |
| 10,274,612 B2 | 4/2019 | Ishii et al. |
| 10,371,647 B2 | 8/2019 | Asai |
| 10,473,801 B2 | 11/2019 | Kawanabe et al. |
| 10,537,295 B2 | 1/2020 | Watanabe et al. |
| 2010/0245378 A1 | 9/2010 | Matsuura |
| 2011/0317054 A1 | 12/2011 | Kameshima et al. |
| 2013/0336452 A1 | 12/2013 | Matsuda et al. |
| 2013/0342514 A1 | 12/2013 | Yokoyama et al. |
| 2014/0014845 A1 | 1/2014 | Sato |
| 2014/0151769 A1 | 6/2014 | Wayama et al. |
| 2014/0154833 A1 | 6/2014 | Wayama et al. |
| 2014/0239186 A1 | 8/2014 | Sato et al. |
| 2014/0361189 A1 | 12/2014 | Kameshima et al. |
| 2015/0192684 A1* | 7/2015 | Ito ........................ G01T 7/005 250/362 |
| 2016/0270755 A1 | 9/2016 | Takenaka et al. |
| 2016/0370304 A1 | 12/2016 | Asai |
| 2018/0008215 A1 | 1/2018 | Wayama et al. |
| 2018/0317868 A1 | 11/2018 | Terui et al. |
| 2018/0328862 A1 | 11/2018 | Sato et al. |

FOREIGN PATENT DOCUMENTS

| | | |
|---|---|---|
| CN | 102480601 A | 5/2012 |
| CN | 104685374 A | 6/2015 |
| JP | 2012-015913 A | 1/2012 |
| JP | 2012-052896 A | 3/2012 |
| JP | 2014-016343 A | 1/2014 |
| JP | 2016-111432 A | 6/2016 |
| JP | 2017-006382 A | 1/2017 |

OTHER PUBLICATIONS

U.S. Appl. No. 16/180,756, filed Nov. 5, 2019, Masato Ofuji.
U.S. Appl. No. 16/443,208, filed Jul. 17, 2019, Keigo Yokohama.
U.S. Appl. No. 16/594,611, filed Oct. 7, 2019, Kazuya Furumoto.
U.S. Appl. No. 16/672,824, filed Nov. 4, 2019, Sho Sato.
U.S. Appl. No. 16/686,589, filed Nov. 18, 2019, Kentaro Fujiyoshi.
U.S. Appl. No. 16/720,989, filed Dec. 19, 2019, Katsuro Takenaka.

* cited by examiner

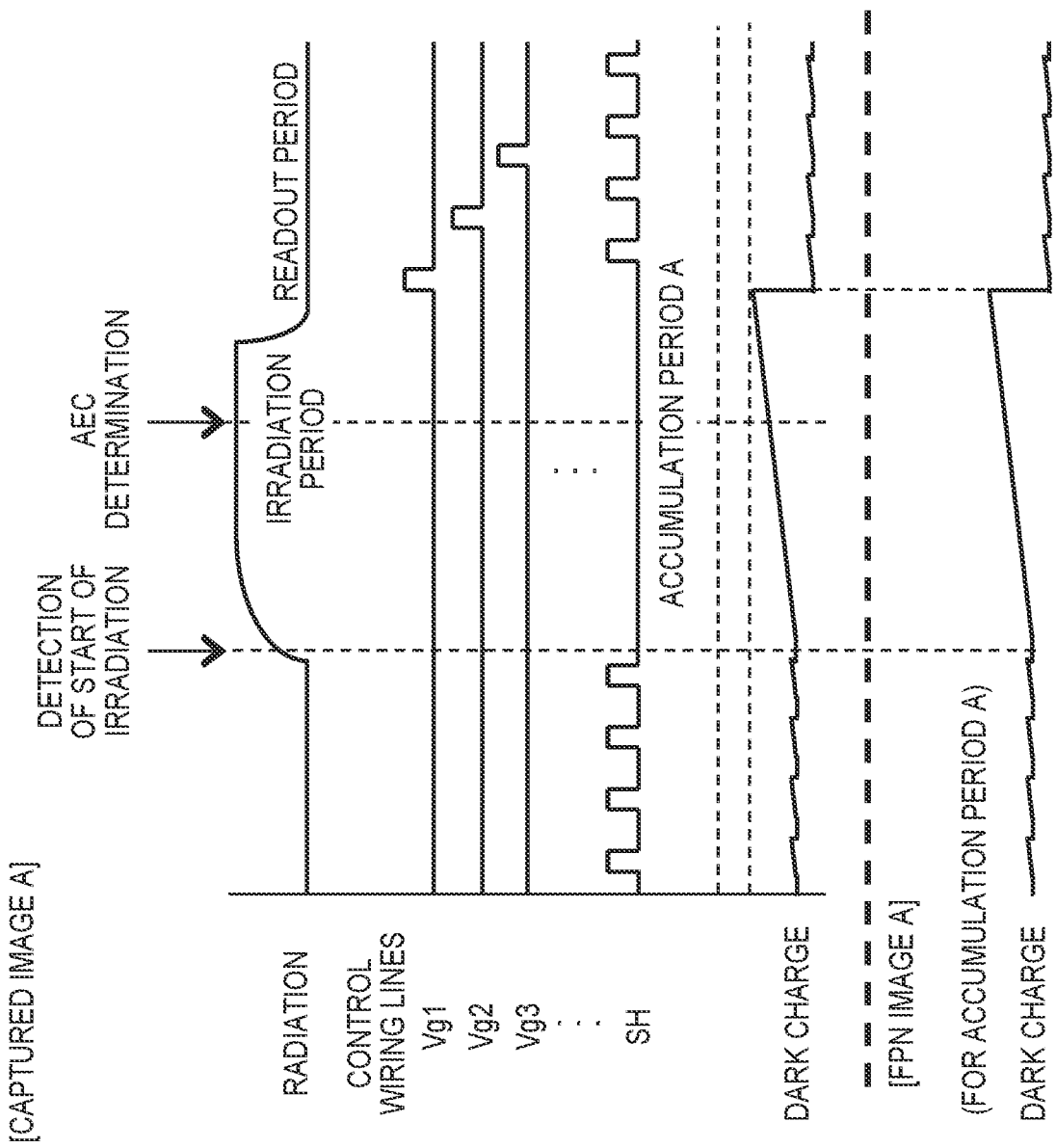

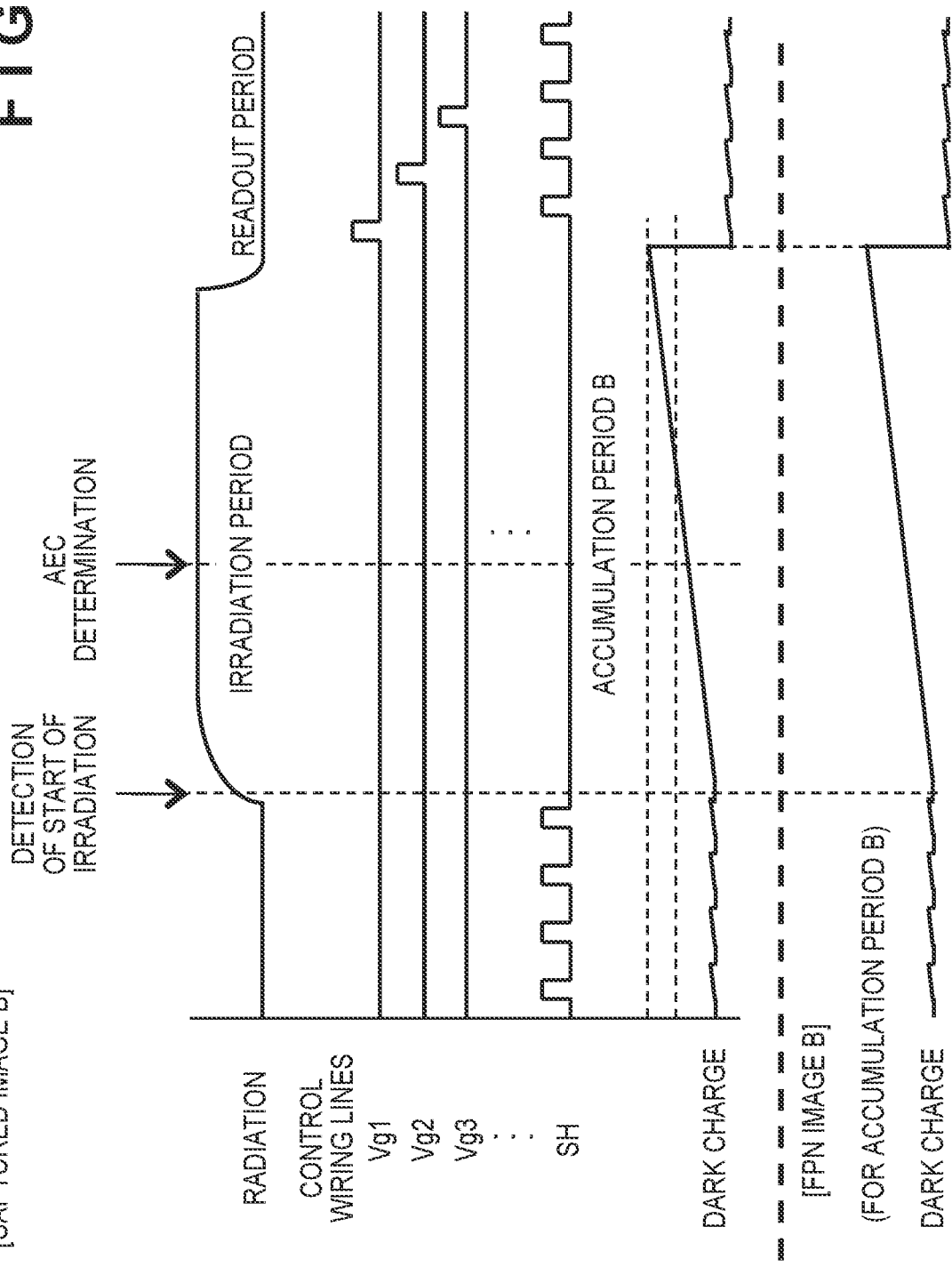

RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

CROSS-REFERENCE TO RELATED APPLICATIONS

This application is a continuation of International Patent Application No. PCT/JP2018/005055 filed on Feb. 14, 2018, and claims priority to Japanese Patent Application No. 2017-075447 filed on Apr. 5, 2017, the entire content of both of which is incorporated herein by reference.

BACKGROUND OF THE INVENTION

Field of the Invention

The present invention relates to a radiation imaging apparatus, a radiation imaging system, a control method of the radiation imaging apparatus, and a non-transitory computer-readable storage medium.

Description of the Related Art

A radiation imaging apparatus that includes an imaging panel in which pixels, each formed by combining a conversion element which converts radiation into charges and a switch element such as a thin film transistor (TFT) or the like, are arrayed is widely used as an imaging apparatus for medical image diagnosis and nondestructive inspection. It is known that irradiation information of radiation that enters the radiation imaging apparatus is obtained in such a radiation imaging apparatus. In Japanese Patent Laid-Open No. 2012-15913 and Japanese Patent Laid-Open No. 2012-52896, it is shown that the detection of the start and the end of a radiation irradiation operation and the detection of the dose of the radiation that entered the apparatus during the radiation irradiation operation are performed.

In a case in which a radiation image is to be obtained by detecting the start of radiation irradiation without synchronizing with a radiation source such as in the case of portable imaging, it may be difficult to grasp the timing at which the radiation irradiation will be executed in advance. Also, in a case in which automatic exposure control (AEC) in which the radiation irradiation is stopped in accordance with a target dose by detecting the dose of incident radiation during the radiation irradiation is to be performed, the radiation irradiation time cannot be preset, and the irradiation time changes depending on the imaging conditions.

Meanwhile, when a radiation image is to be obtained, the level of an offset arising from a signal processing circuit or the conversion element for converting the incident radiation into charges needs to be corrected for each signal output from each pixel. If the charge accumulation time changes in the conversion element, the offset level will change due to a dark current generated in the conversion element. In a case in which an imaging operation in which the radiation irradiation time cannot be preset is to be performed, the image quality of the radiation image obtained by performing offset level correction may degrade since the offset level will change in accordance with the change in the charge accumulation time for each imaging operation. Also, although the charge accumulation time may be set to a predetermined time which is longer than the expected irradiation time in order to prevent the offset level from changing, charge accumulation will continue even after the radiation irradiation operation has been completed in this case, and there will be a wait time until the image will be displayed after the end of the radiation irradiation operation.

Some embodiments of the present invention provide a technique advantageous in an imaging operation in which a radiation irradiation time cannot be preset.

SUMMARY OF THE INVENTION

According to some embodiments, a radiation imaging apparatus comprising: an imaging region in which a plurality of conversion elements are arranged, wherein the plurality of conversion elements includes a first conversion element configured to obtain a radiation image and a second conversion element configured to obtain irradiation information of incident radiation during radiation irradiation; a storage unit configured to store correction data for correcting a signal output from the first conversion element; and a control unit, wherein the control unit determines a period to cause the first conversion element to perform an accumulation operation in accordance with the irradiation information, determines a correction amount corresponding to the period based on the correction data, and generates a radiation image signal by correcting a signal output from the first conversion element in accordance with the correction amount after the radiation irradiation, is provided.

According to some other embodiments, a control method of a radiation imaging apparatus comprising an imaging region in which a plurality of conversion elements are arranged, wherein the plurality of conversion elements includes a first conversion element configured to obtain a radiation image and a second conversion element configured to obtain irradiation information of incident radiation during radiation irradiation, and a storage unit configured to store correction data for correcting a signal output from the first conversion element, the method comprises: determining a period to cause the first conversion element to perform an accumulation operation in accordance with the irradiation information; determining a correction amount corresponding to the period based on the correction data; and generating a radiation image signal by correcting a signal output from the first conversion element in accordance with the correction amount after the radiation irradiation, is provided.

According to still other embodiments, a non-transitory computer-readable storage medium storing a program for causing a computer to execute a control method for controlling a radiation imaging apparatus comprising an imaging region in which a plurality of conversion elements are arranged, wherein the plurality of conversion elements includes a first conversion element configured to obtain a radiation image and a second conversion element configured to obtain irradiation information of incident radiation during radiation irradiation, and a storage unit configured to store correction data for correcting a signal output from the first conversion element, the method comprises: determining a period to cause the first conversion element to perform an accumulation operation in accordance with the irradiation information; determining a correction amount corresponding to the period based on the correction data; and generating a radiation image signal by correcting a signal output from the first conversion element in accordance with the correction amount after the radiation irradiation, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3A is a timing chart of an operation of the radiation imaging apparatus of FIG. 1;

FIG. 3B is a timing chart of an operation of the radiation imaging apparatus of FIG. 1;

DESCRIPTION OF THE EMBODIMENTS

Detailed embodiments of a radiation imaging system according to the present invention will be described hereinafter with reference to the accompanying drawings. Note that radiation according to the present invention can include not only α-rays, β-rays, and γ-rays that are beams generated by particles (including photons) emitted by radioactive decay, but also beams that have equal or more energy, for example, X-rays, particle rays, and cosmic rays.

Figure 1:
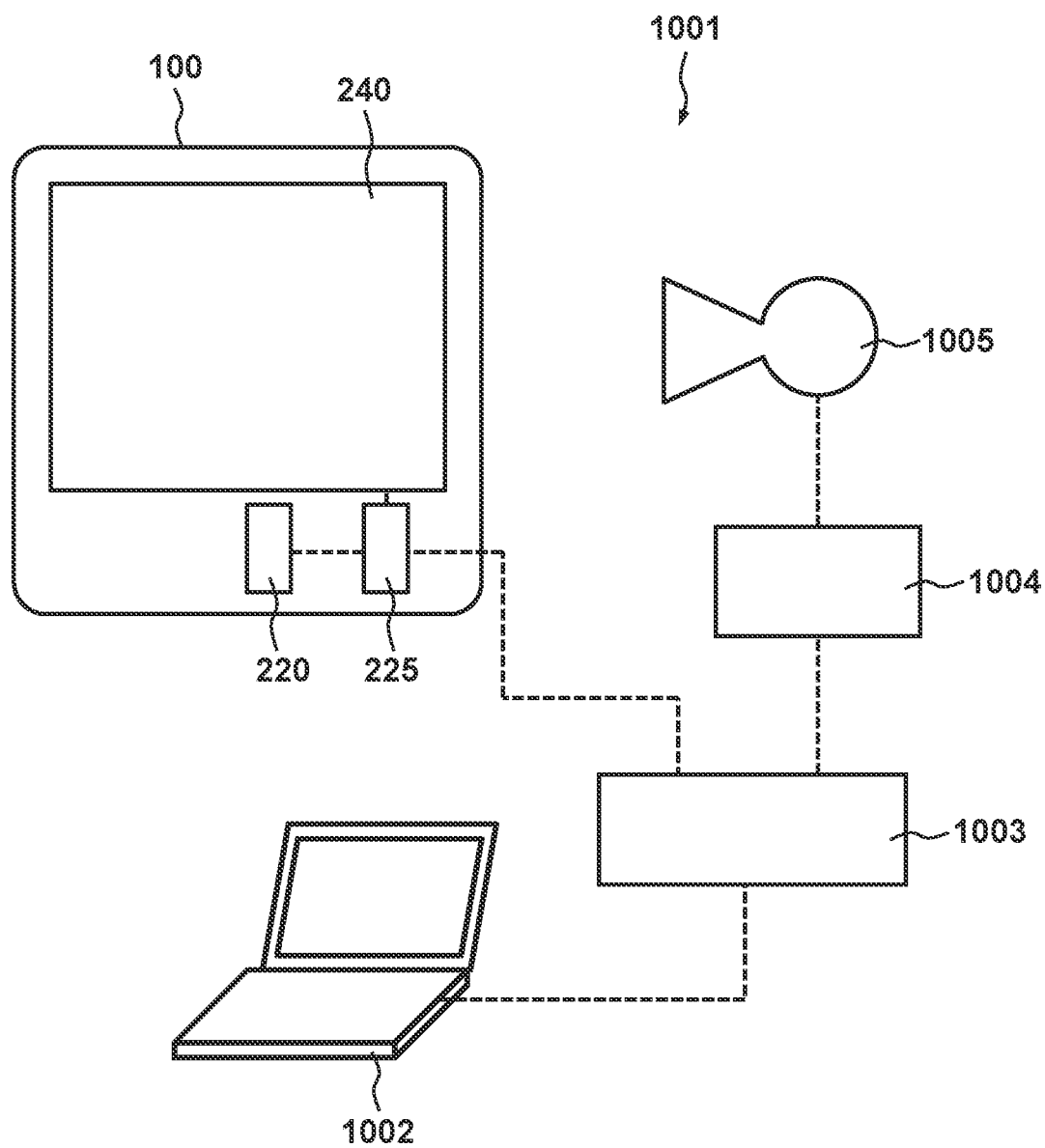
FIG. 1 is a view showing an example of the arrangement of a system using a radiation imaging apparatus according to an embodiment of the present invention.

The arrangement of a radiation imaging apparatus according to an embodiment of the present invention will be described with reference to FIGS. 1 to 10. FIG. 1 is a view showing an example of the arrangement of a system 1001 related to automatic exposure control (AEC) using a radiation imaging apparatus 100 according to a first embodiment of the present invention. The system 1001 includes the radiation imaging system 100, a control system 1002, a communication relay system 1003, a radiation interface 1004, and a radiation source 1005. The radiation imaging apparatus 100 includes a detection unit 240 in which a plurality of pixels for obtaining a radiation image are arranged, a control unit 225 that controls the detection unit 240, and a storage unit 220. These components are communicably connected to each other via wired or wireless communication, and the communication delay between the components is set as a managed value in accordance with the method and communication contents.

An operation performed when an image of an object is to be captured by using an AEC function in the system 1001 will be described next. Before imaging of the object, a user (for example, a doctor, a technologist, or the like) uses the control system 1002 to make an input to stop the radiation source 1005 when the accumulated value of a radiation dose reaches a predetermined dose A. In addition, the user uses the control system 1002 to designate a region of interest (ROI) from which the dose of incident radiation is to be detected. The user also uses the control system 1002 to input an irradiation time B [ms], a tube current C [mA], and a tube voltage D [kV] which are conditions by which the radiation source 1005 is to execute a radiation irradiation operation. These conditions may be suitably selected from a recipe already stored in a memory incorporated in the control system 1002 or may be input separately.

Next, when the user presses an exposure switch provided in the control system 1002 or the radiation source 1005, the radiation imaging apparatus 100 is irradiated with radiation via an object. In the radiation imaging apparatus 100, when the accumulated value of radiation dose obtained in the ROI designated by the user via the control system 1002 reaches a dose A', the control unit 225 outputs a radiation exposure stop signal. The radiation exposure stop signal output from the control unit 225 is transmitted to the radiation source 1005 via the communication relay system 1003 and the radiation interface 1004. The radiation source 1005 stops the radiation irradiation in response to this radiation exposure stop signal. The dose A' in this case can be a value calculated in consideration of the dose A, the intensity of radiation irradiation, the communication delay between the components, and the processing delay. In addition, if the irradiation time B [ms] set by the user has arrived, the radiation source 1005 will stop the radiation irradiation regardless of the presence or absence of the radiation exposure stop signal that is output from the control unit 225. This embodiment will describe a case in which the control unit 225 will output a radiation exposure stop signal when the control unit 225 measures the dose of incident radiation and determines that the accumulated value of the dose of incident radiation has reached a predetermined threshold. However, the present invention is not limited to this. The control unit may be used to only measure (monitor) the dose of radiation that entered the radiation imaging apparatus 100, and the control system 1002 may calculate the accumulated value of the dose obtained by the radiation imaging apparatus 100 and output the signal to control the exposure. Furthermore, the control unit 225 may be used not only for AEC, but also for an automatic radiation irradiation start detection technique for detecting the start of radiation irradiation and for an automatic radiation irradiation end detection technique for detecting the end of radiation irradiation.

Figure 2:
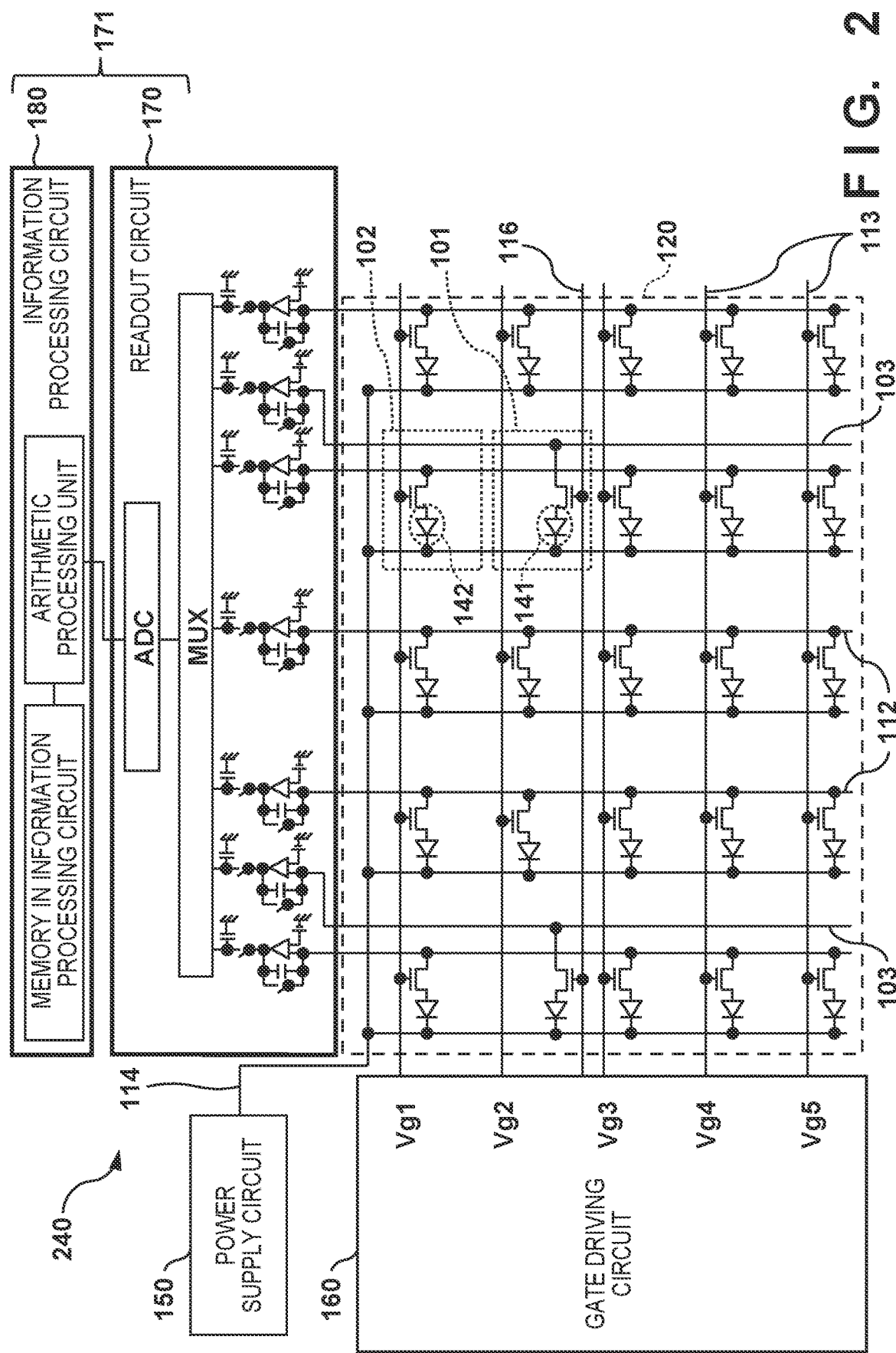
FIG. 2 is a circuit diagram showing an example of the circuit arrangement of a detection unit of the radiation imaging apparatus of FIG. 1.

FIG. 2 is an equivalent circuit diagram showing an example of the circuit arrangement of the detection unit 240 of the radiation imaging apparatus 100. The detection unit 240 includes an imaging region 120 in which a plurality of pixels each including one of conversion elements 141 and 142 for converting radiation into electrical signals on a substrate, and a peripheral region for controlling the pixels and the electrical signals output from the pixels.

The peripheral region includes a power supply circuit 150 and a gate driving circuit 160 for controlling and driving each pixel and a signal processing circuit 171 which includes a readout circuit 170 and an information processing circuit 180 for processing the electrical signal output from each pixel. However, the arrangement of the peripheral region is not limited to this. For example, the readout circuit 170 and the information processing circuit 180 may be integrally formed.

The imaging region 120 includes a plurality of pixels 102 for obtaining a radiation image and one or more detection pixels 101 for detecting radiation irradiation and obtaining irradiation information during the radiation irradiation. Each detection pixel 101 is used to obtain irradiation information which is information related to incident radiation such as the start of radiation irradiation and the end of radiation irradiation, the intensity of radiation irradiation, the radiation irradiation dose, and the like. In other words, a plurality of conversion elements are arranged on the imaging region 120, and the plurality of conversion elements include conversion elements 142 for obtaining a radiation image and conversion elements 141 for obtaining irradiation information of incident radiation. Although a pixel matrix of 5 rows and 5 columns is arranged in the imaging region 120 shown in FIG. 1, the number of pixels is not limited to this.

Power is supplied from the power supply circuit 150 to each pixel 102 arranged in the imaging region of the radiation imaging apparatus 100 via a power supply wiring line 114, and each pixel is controlled by the gate driving circuit 160 via a corresponding one of image control wiring lines 113. The signal output from the conversion element 142 of each pixel 102 is transferred to the signal processing circuit 171 via a corresponding one of image signal lines 112. As a result, a radiation image can be obtained. Also, power is supplied from the power supply circuit 150 to each detection pixel 101 via the power supply wiring line 114, and each detection pixel is controlled by the gate driving circuit 160 via a detection control wiring line 116. A signal output from the conversion element 141 of each detection pixel 101 is transferred to the signal processing circuit 171 via a corresponding one of detection signal lines 103. Irradiation information such as the dose of radiation that entered each region where the detection pixel 101 is arranged can be obtained by obtaining the radiation irradiation information by using the detection pixel 101. In this embodiment, the detection signal lines 103 are arranged inside the imaging region 120. However, the detection signal lines 103 may be arranged adjacent to the outer edge of the imaging region 120.

In the system 1001, the intensity of radiation entering the radiation imaging apparatus 100 changes greatly depending on the specifications of the radiation source 1005. For example, although an imaging operation may require radiation irradiation of about 100 ms to 1,000 ms if the radiation source 1005 having a small output is used, a radiation image can be obtained by executing radiation irradiation of about 1 ms to 10 ms if a radiation source having a large output is used. In a case in which the radiation source changes for each imaging operation such as the case of portable imaging or in a case in which an imaging operation without a preset radiation irradiation time such as the case of imaging using an AEC function is to be performed, the following problems may occur.

Figure 4A:
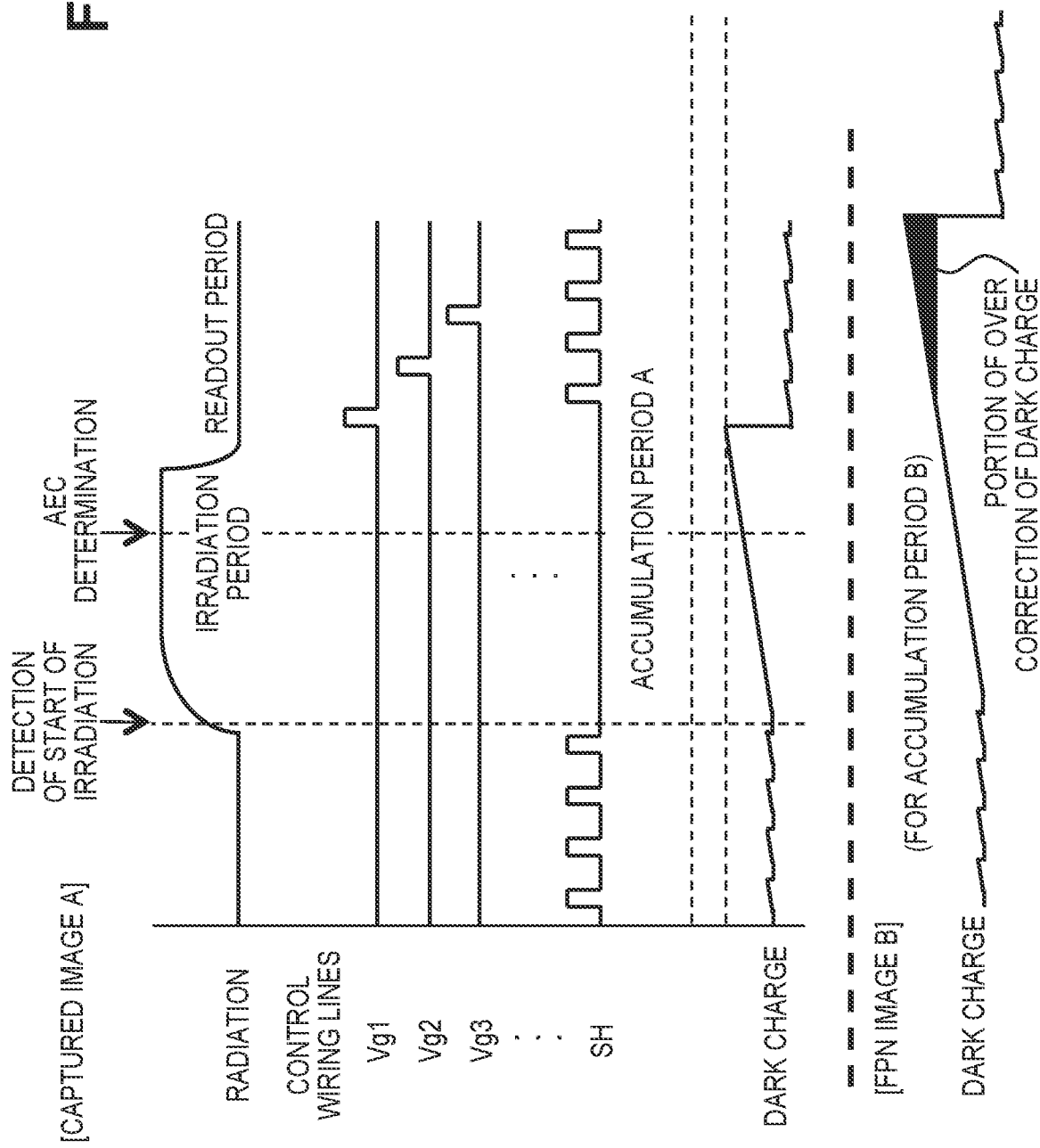
FIG. 4A is a timing chart of an operation of a radiation imaging apparatus of a comparative example.
Figure 4B:
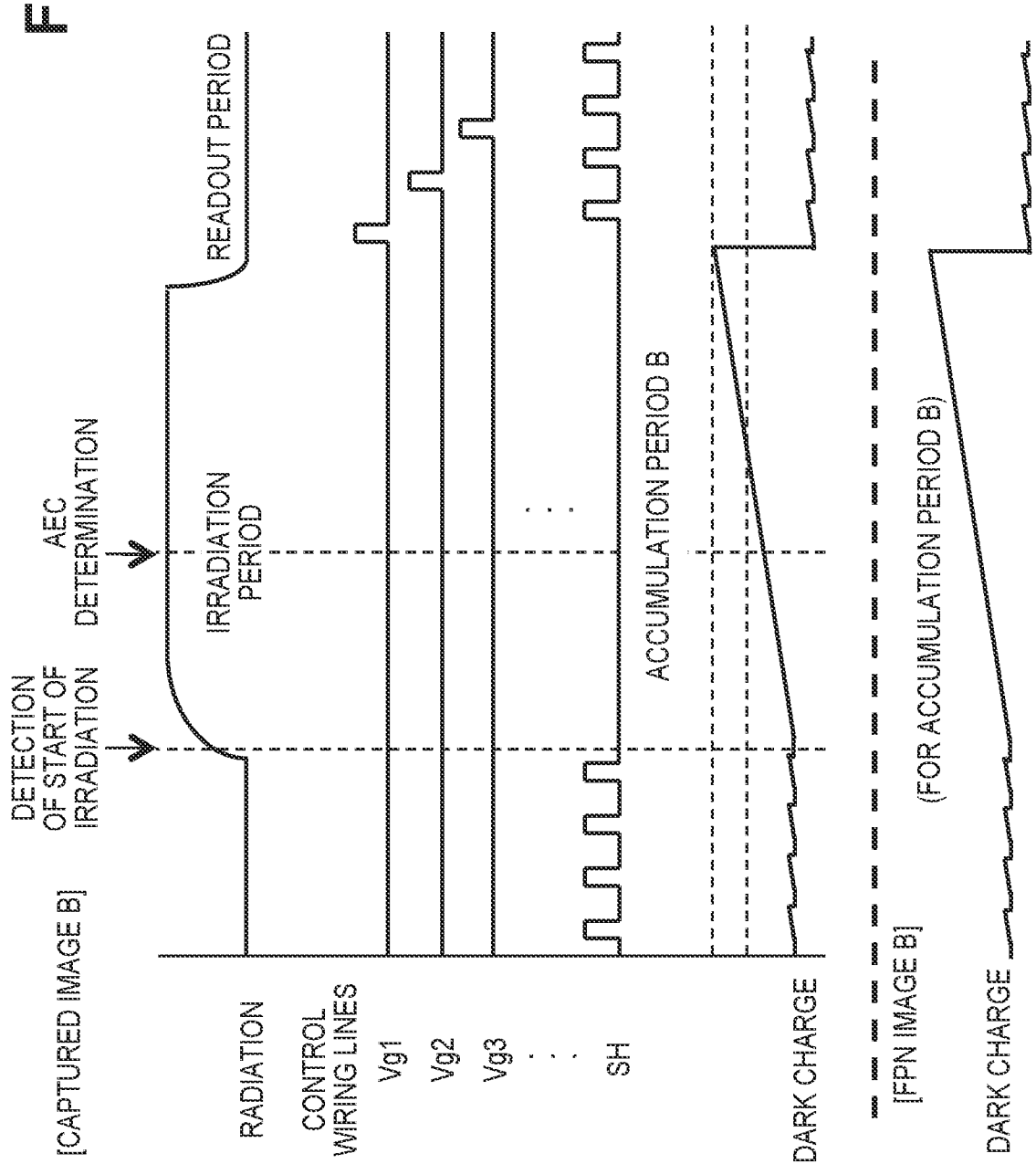
FIG. 4B is a timing chart of an operation of the radiation imaging apparatus of the comparative example.

FIGS. 4A and 4B are timing charts of a comparative example of the embodiment when a radiation image is to be obtained. FIG. 4A shows a timing chart in a case in which the radiation source 1005 has a higher output than in the case of FIG. 4B, the radiation irradiation period is shorter than that of FIG. 4B, and the period in which the charge accumulation operation performed by the conversion element 142 of each pixel 102 is short. In contrast to the case of FIG. 4A, FIG. 4B shows a timing chart of a case in which the charge accumulation operation performed by the conversion element 142 of each pixel 102 is long. Since the offset level will change due to a dark current generated in the conversion element 142 when the charge accumulation time of the conversion element 142 is changed, offset level correction needs to be performed on a signal obtained by radiation irradiation. Consider a case in which offset level correction is performed by using the same correction amount for a case with a short charge accumulation period as shown in FIG. 4A and a case with a long charge accumulation period as shown in FIG. 4B. In the case shown in FIG. 4A, correction is performed by using a correction amount according to the case of FIG. 4B with the long charge accumulation period. In this case, as shown in FIG. 4A, correction amount becomes larger than the amount of the offset caused by the dark current generated during an imaging operation with a short radiation irradiation period and a short charge accumulation period. Hence, this may generate a difference between the actual amount of the offset and the correction amount used for offset level correction, and may degrade the image quality of the radiation image obtained through the offset correction. For example, since a dark current can vary on the surface of each pixel 102 of the imaging region 120, it may appear as an artifact on an obtained radiation image.

Figure 5A:
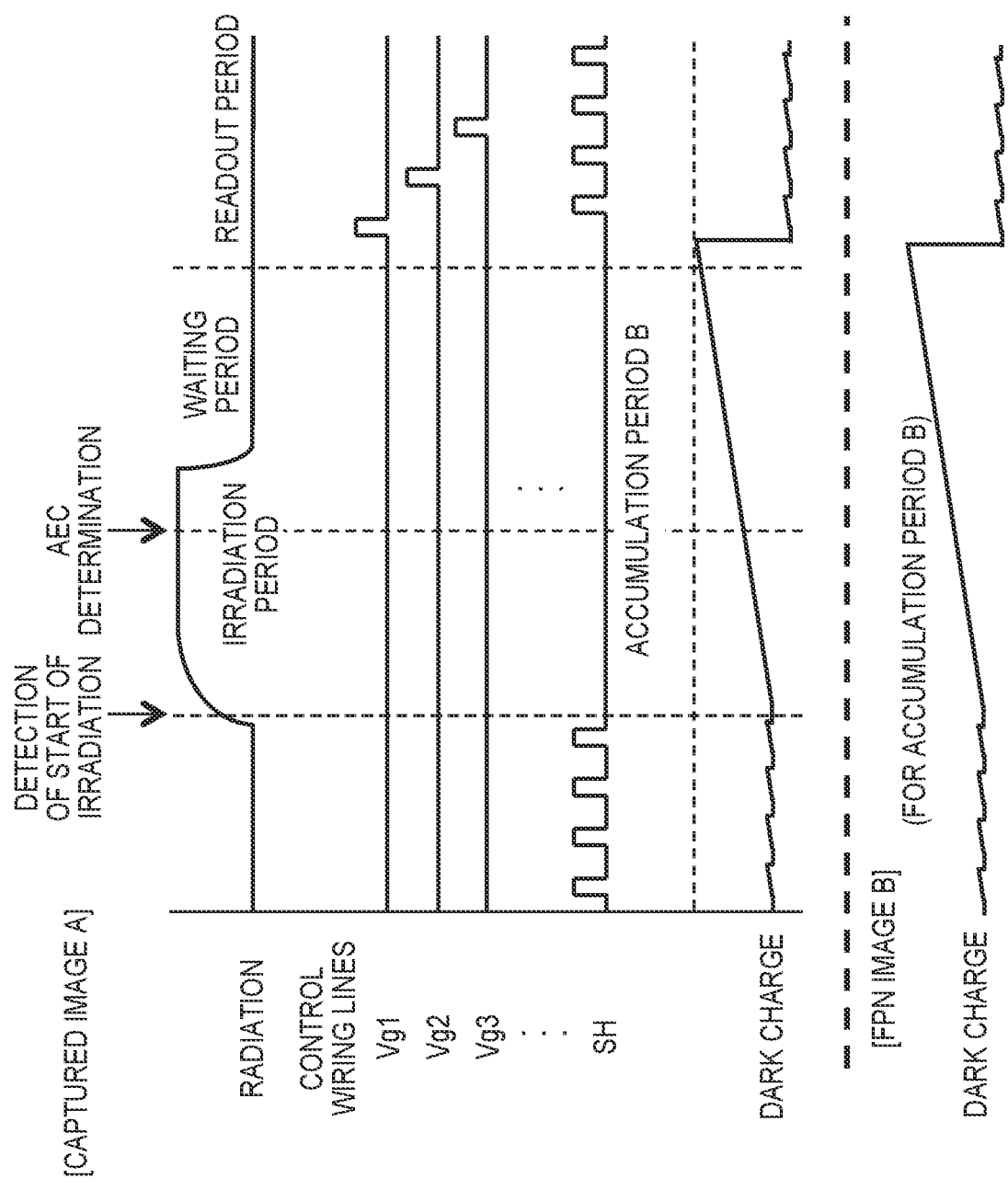
FIG. 5A is a timing chart of an operation of a radiation imaging apparatus of a comparative example.
Figure 5B:
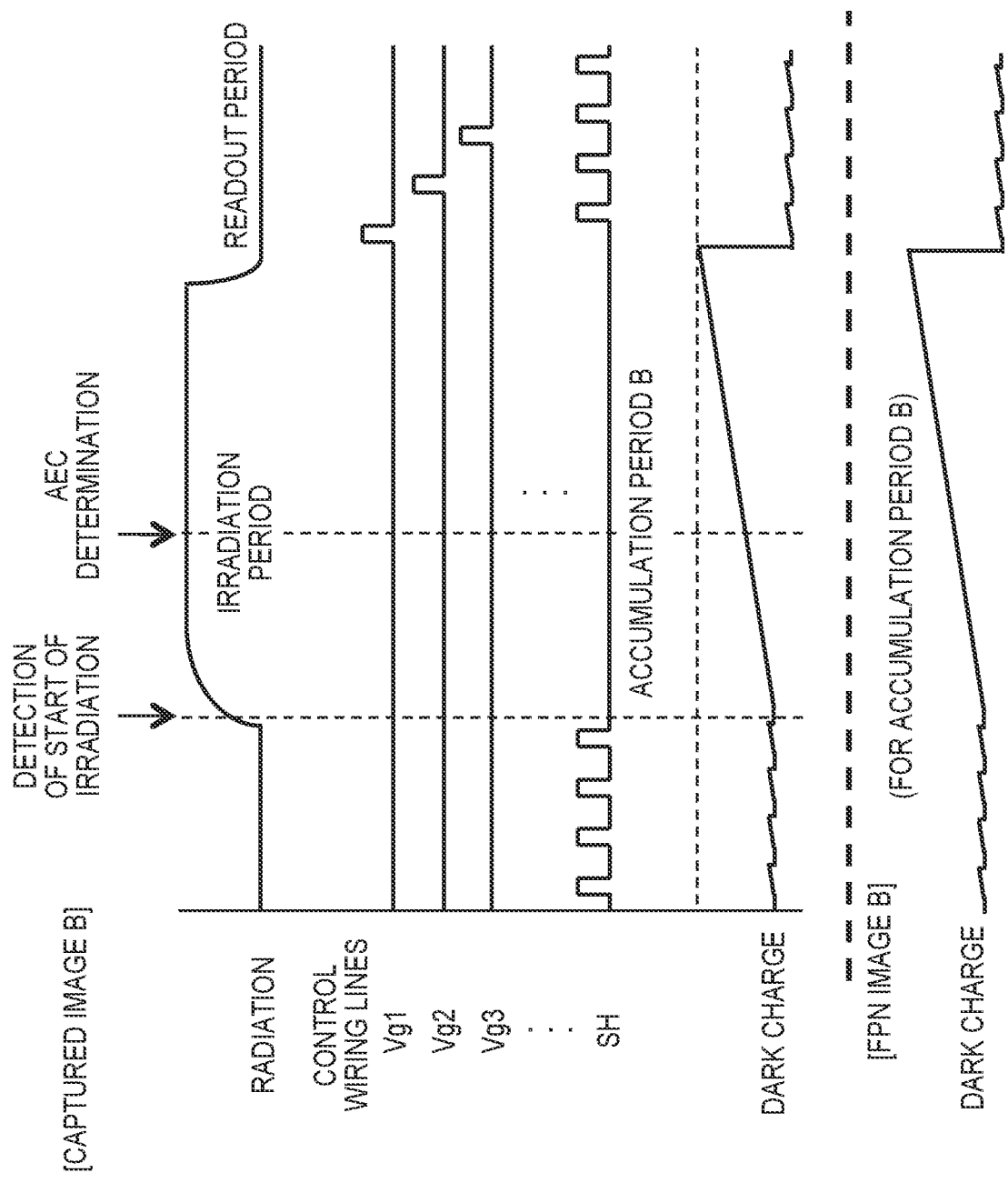
FIG. 5B is a timing chart of an operation of the radiation imaging apparatus of the comparative example.

FIGS. 5A and 5B are timing charts of another comparative example for suppressing image quality degradation of an obtained radiation image while performing offset level correction by using the same correction amount. In an imaging operation shown in FIG. 5A which has a shorter radiation irradiation time than in the case of FIG. 5B, the accumulation operation period for accumulating charges is set to be long in a similar manner to that in the case of FIG. 5B, and correction is performed after the imaging operation by using the same correction amount. In the case of the imaging operation shown in FIG. 5B, the correction amount used to perform offset level correction is an amount suitable for the accumulation operation period. However, in a case in which imaging is to be performed at a timing as shown in FIG. 5A, for example, if correction is to be performed by using a correction amount that is used for a case in which charges are accumulated for 1000 ms even when the radiation irradiation operation has been completed in 2 ms, a wait time of 998 ms (about 1 sec) would need to be set after the radiation irradiation operation. As a result, it will delay, for example, the preview image display which is performed after the correction for the user to confirm whether the radiation image has been obtained or the start of transferring of captured image data, and degrade the usability of the radiation imaging apparatus.

Next, the operation of the radiation imaging apparatus 100 according to this embodiment will be described with reference to the timing charts shown in FIGS. 3A and 3B. In order to perform suitable offset level correction even if the charge accumulation period of the conversion elements of pixels 102 changes when executing an imaging operation without a constant radiation irradiation time, the radiation imaging apparatus 100 of this embodiment operates in accordance with the timing charts shown in FIGS. 3A and 3B.

FIG. 3A shows a timing chart of a case in which the intensity of the radiation irradiation is high and the radiation irradiation is stopped after a short time as a result of AEC determination. FIG. 3B shows a timing chart of a case in which the intensity of the radiation irradiation is lower than that in the case of FIG. 3A and the radiation irradiation is stopped after a long period of time as a result of AEC determination.

When radiation irradiation is executed, the control unit 225 stops the readout operation of a sampling circuit of the readout circuit 170 which is indicated by reference symbol SH in FIGS. 3A and 3B. In addition, the control unit 225 causes the charge accumulation operation for accumulating charges corresponding to the incident radiation to be started in the conversion element of each pixel 102 via the corresponding image control wiring line 113. More specifically, signals Vg (Vg1, Vg2, Vg3 . . . ) of the respective image control wiring lines 113 shown in FIGS. 3A and 3B are set at low level. Among the pieces of radiation irradiation information, the radiation irradiation start information may be obtained by, for example, causing the control system 1002 to simultaneously output a radiation irradiation instruction signal to the radiation source 1005 and the control unit 225. The automatic radiation irradiation start detection technique for detecting the start of radiation irradiation may be used by the control unit 225 based on a signal output from each conversion element 141 by sampling the signal output from the conversion element 141 of each detection pixel 101. In addition, the control unit 225 may sequentially set the signals Vg of the respective image control wiring lines 113 at high level to reset the charges accumulated in the conversion elements 142 of the pixels 102 before obtaining the radiation irradiation start information.

After the radiation irradiation has been started, the control unit 225 samples the signal output from the conversion element 141 of each detection pixel 101, and executes AEC determination by using the information of the dose of incident radiation among the pieces of radiation irradiation information based on the signal output from the conversion element 141. The control unit 225 determines the time to stop the radiation irradiation by obtaining the accumulated value of the dose of the incident radiation, and outputs a radiation exposure stop signal. For example, the control unit may output the signal to stop the exposure in response to the accumulated value of the dose of the incident radiation reaching a predetermined threshold. The radiation source 1005 stops the radiation irradiation operation in response to the radiation exposure stop signal. In addition to outputting the signal to stop the radiation irradiation operation, the control unit 225 ends the accumulation operation of each pixel 102 and sequentially sets the signals Vg of the respective image control wiring lines 113 connected to the gate driving circuit 160 at high level. As a result, a signal corresponding to charges accumulated in the conversion element 142 of each pixel 102 is output. In this manner, the control unit 225 uses, among the pieces of radiation irradiation information, the radiation irradiation start information and the information of the dose of incident radiation to determine the charge accumulation operation period of the conversion element 142 of each pixel 102.

It can be determined from the result of the AEC determination that the radiation irradiation time is longer in the case of FIG. 3B than in the case of FIG. 3A. Hence, the charge accumulation period of the conversion element 142 of each pixel 102 becomes longer and more dark charges are generated in the case of FIG. 3B than in the case of FIG. 3A. As a result, the offset level of the signal output from the conversion element 142 of each pixel 102 changes between the operation shown in FIG. 3A and the operation shown in FIG. 3B. Hence, in order to perform correction by using a correction amount that corresponds to the accumulation operation period in which charges were accumulated, the control unit 225 determines the correction amount corresponding to the charge accumulation period based on the correction data which is used for executing offset correction and is obtained and stored in advance in the storage unit 220. For example, a plurality of correction coefficients corresponding to respective accumulation operation periods are stored as correction data in the storage unit 220, and the control unit 225 may select one correction coefficient that corresponds to the charge accumulation period. In this case, if there is a correction coefficient of a period which is identical to the actual charge accumulation period, the control unit may select this correction coefficient. In a case in which there is no correction coefficient with an identical charge accumulation period, a correction coefficient of a period near the actual accumulation operation period may be selected. In addition, for example, the plurality of correction coefficients may be combined to generate a simulation correction amount of the accumulation operation period of the actual imaging operation. Also, for example, a single function may be stored as a correction coefficient in the storage unit 220, and the control unit 225 may generate an appropriate correction amount from this function in accordance with the charge accumulation period. After the radiation irradiation operation, the signal output from the conversion element 142 of each pixel 102 is corrected in accordance with the correction amount determined by the control unit 225 in the manner described above to generate a radiation image signal. The correction coefficient may be a different value for each of the conversion elements 142 of the pixels 102 in the imaging region 120, and the storage unit 220 may store a plurality of correction coefficients for the conversion element 142 of each pixel 102.

Although the control unit 225 executed the AEC determination and controlled the radiation irradiation time and the accumulation operation period for accumulating charges in the conversion element 142 of each pixel 102 in this embodiment, the control of the accumulation operation period is not limited to this. For example, the control system 1002 may control the radiation irradiation period. In such a case, the control unit 225 may obtain the radiation irradiation start information or the radiation irradiation end information by receiving a signal for controlling the radiation source 1005 from the control system 1002, and determine the accumulation period for accumulating charges in the conversion element 142 of each pixel 102. The automatic radiation irradiation start/end detection techniques in which the control unit 225 obtains the radiation irradiation start/end information of the radiation irradiation information based on the signal output from the detection pixels 101 may be used. The control unit 225 will detect the start of radiation irradiation by sampling the signal from the conversion element 141 of each detection pixel 101, and cause the conversion element 142 of each pixel 102 to start the accumulation operation in response to the detection. In addition, the control unit will detect the end of radiation irradiation based on the signal output from each conversion element 141 by sampling the signal output from the conversion element 141 of each detection pixel 101, and cause the conversion element 142 of each pixel 102 to end the accumulation operation in response to the detection. Next, the control unit 225 causes the conversion element 142 of each pixel 102 to output a signal. Furthermore, for example, the control unit 225 may determine the radiation irradiation time in accordance with the correction amount stored in the storage unit 220. In this case, after obtaining the radiation irradiation start information, the control unit 225 can output a radiation exposure stop signal according to the determined irradiation time while ending the accumulation operation executed in the conversion element 142 of each pixel 102, and cause signals to be output from the respective conversion elements 142.

Figure 6:
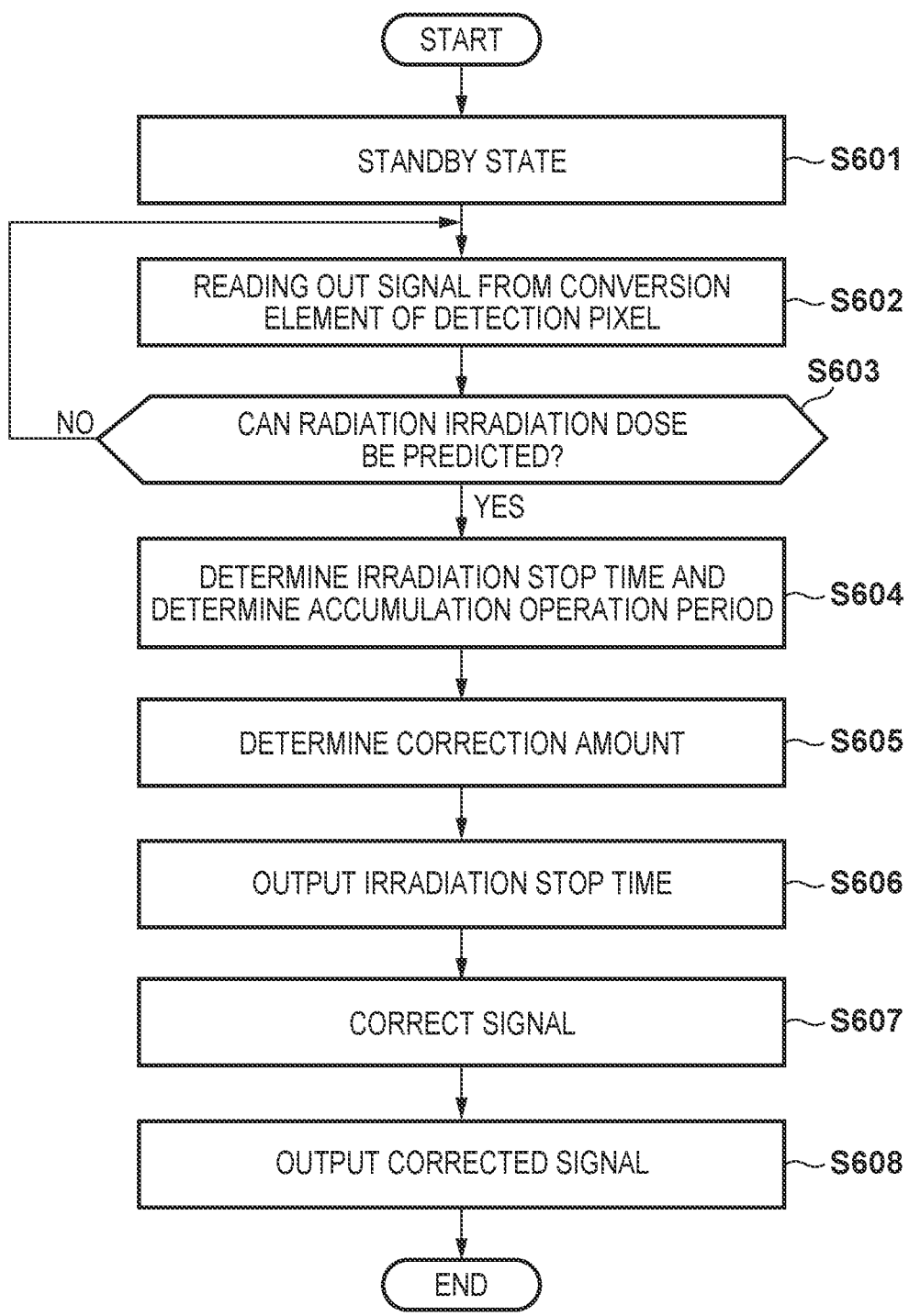
FIG. 6 is a flowchart of the radiation imaging apparatus of FIG. 1.

FIG. 6 is a flowchart for stopping radiation irradiation and determining an offset level correction amount after the control unit 225 has performed AEC determination in the radiation imaging apparatus 100 according to this embodiment. First, in step S601, the radiation imaging apparatus 100 is in a standby state. Next, after obtaining the radiation irradiation start information, the control unit 225 reads out, in step S602, a signal from the conversion element 141 of each detection pixel 101. Next, in step S603, the control unit 225 determines whether the accumulated value of the dose of incident radiation can be predicted. If the accumulated value of the dose of incident radiation cannot be predicted, the control unit 225 returns the process to step S602. The process advances to step S604 at the stage in which the accumulated value of the dose of incident radiation can be predicted, and the control unit calculates and determines the radiation irradiation stop time. In addition, in the process of determining the radiation irradiation time in step S604, the control unit 225 determines the accumulation operation period for accumulating charges in the conversion element 142 of each pixel 102.

Next, in step S605, the control unit 225 determines the correction amount for correcting the offset level from the correction data stored in the storage unit 220. At this time, the control unit 225 may select, as the correction amount corresponding to the accumulation operation period in which the conversion element 142 of each pixel 102 accumulated charges, a suitable correction coefficient from the correction coefficients stored as the correction data in the storage unit 220. Alternatively, the control unit 225 may generate a suitable correction amount by using various kinds of arithmetic operations based on the correction data stored in the storage unit 220. After the correction amount has been determined, the process advances to step S606 and the control unit 225 outputs the radiation irradiation stop time. In step S607, after the radiation irradiation has ended, the signal output from the conversion element 142 of each pixel 102 is corrected in accordance with the correction amount selected or generated by the control unit 225. Each corrected radiation image signal is output in step S608.

The flowchart shown in FIG. 6 is merely an example of a flowchart of a procedure performed at the time of an actual imaging operation, and the present invention is not limited to this flowchart. For example, the correction amount for offset level correction may be determined (step S605) after a signal for stopping radiation irradiation has been output (step S606).

Figure 7:
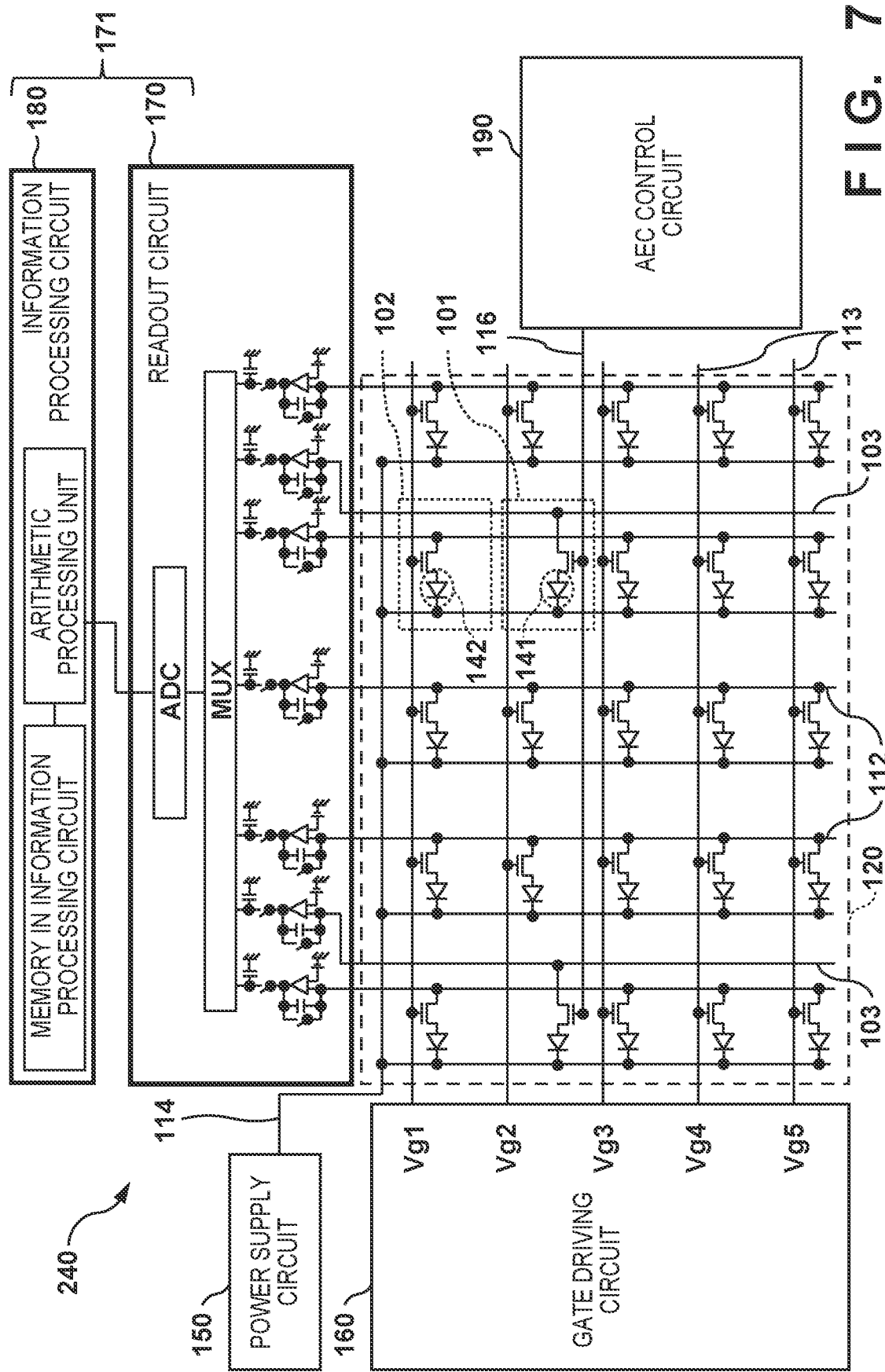
FIG. 7 is a circuit diagram showing a modification of the circuit arrangement of the detection unit of FIG. 2.

FIG. 7 is an equivalent circuit diagram showing the circuit arrangement of the detection unit 240 of the radiation imaging apparatus 100 according to this embodiment, and shows a modification of the circuit arrangement shown in FIG. 2. A point which differs from the equivalent circuit diagram shown in FIG. 2 is that an AEC control circuit 190, which is arranged separately from the gate driving circuit 160 for controlling the pixels 102, is used to control the detection control wiring line 116 for controlling the detection pixels 101. Points other than this may have a circuit arrangement similar to that of the equivalent circuit diagram shown in FIG. 2. As a result of this arrangement, the gate driving circuit 160 need not perform a complex operation compared to that of the gate driving circuit 160 of the detection unit 240 shown in FIG. 2, and the design of the driving circuit can be simplified. For example, a merit of this arrangement is that the sensitivity and the transfer rate of the conversion elements of the detection pixel 101 and those of the conversions of the pixel 102 can be changed freely. It also allows the number of switch elements (for example, thin-film transistors: TFTs) to be connected to each detection signal line 103 to be suppressed to a minimum, thereby allowing the wiring capacity to be reduced, the readout rate to be improved, and the noise to be reduced.

In the case of the circuit arrangement shown in FIG. 7, the AEC control circuit 190 is driven during a period in which, for example, the radiation irradiation is performed and the radiation irradiation information is obtained from the signal output from the conversion element of each detection pixel 101. Next, when signals for obtaining a radiation image are to be read out from the conversion elements of the pixels 102, the AEC control circuit 190 may be stopped, and the gate driving circuit 160 may be driven to sequentially read out a signal for each row. A circuit that causes the circuits in the peripheral region to operate separately for the detection pixels 101 and the pixels 102 is not limited to a control circuit. For example, the signals from the detection signal line 103 and the signals from the pixel 102 may be processed separately by arranging separate readout circuits in the readout circuit 170 of the signal processing circuit 171.

Figure 8A:
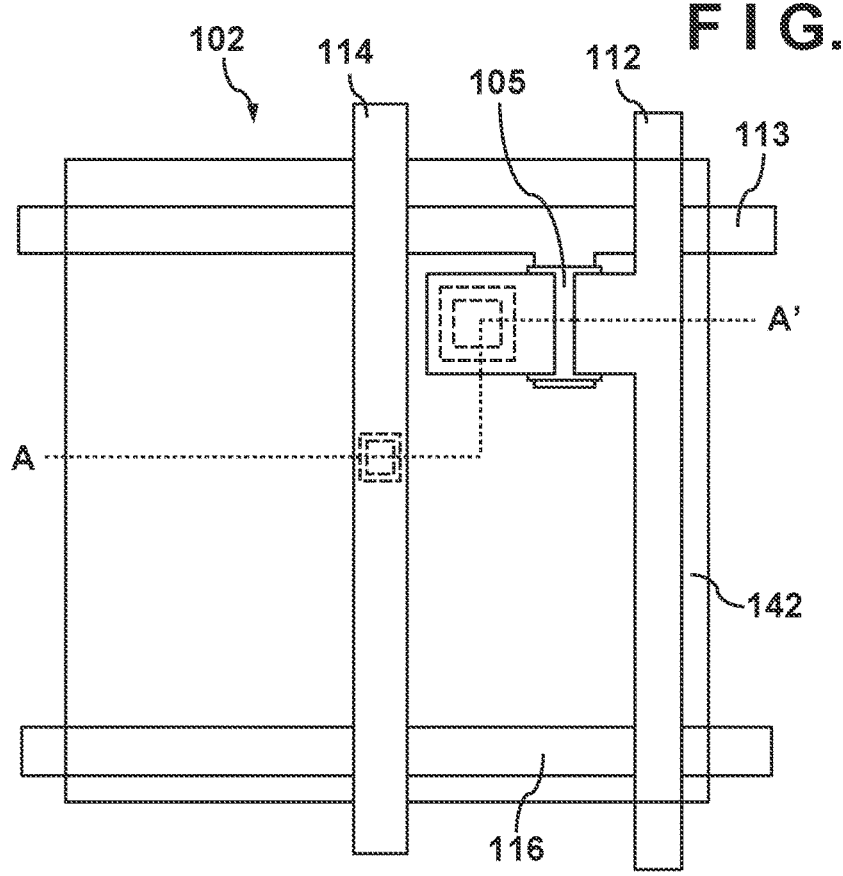
FIG. 8A is a plan view of a pixel of the radiation imaging apparatus of FIG. 1.
Figure 8B:
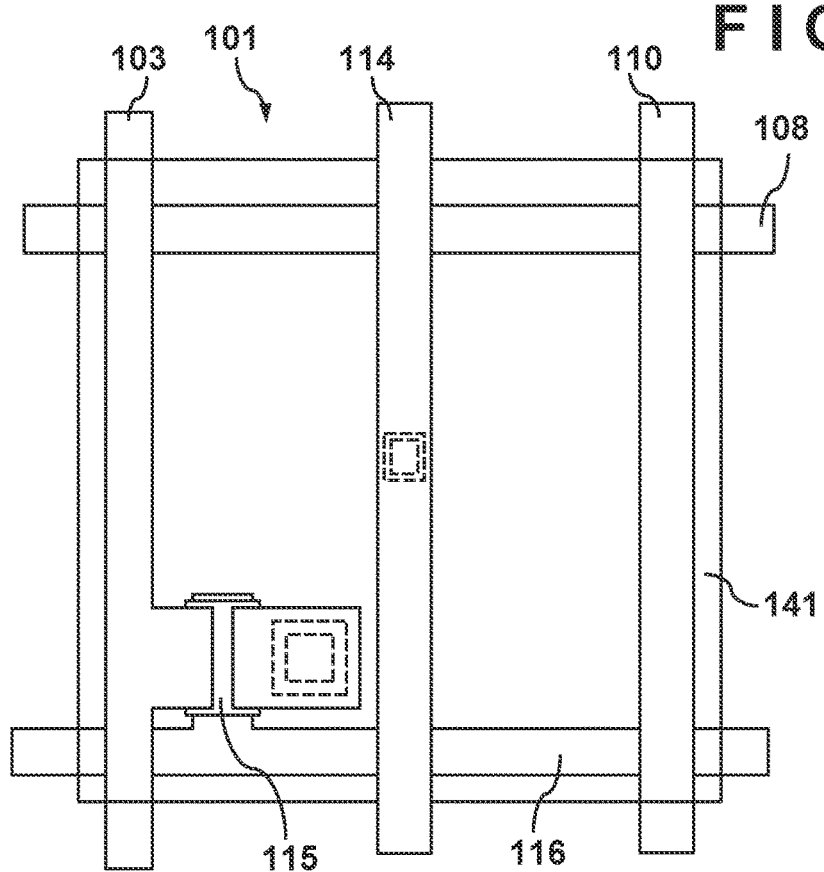
FIG. 8B is a plan view of a detection pixel of the radiation imaging apparatus of FIG. 1.

FIGS. 8A and 8B are plan views of the pixel 102 and the detection pixel 101, respectively. FIG. 8A shows a plan view of the pixel 102. In this embodiment, the radiation imaging apparatus 100 is an indirect-type radiation imaging apparatus, and a scintillator (not shown) is arranged above the imaging region 120 on which the pixels 102 and the detection pixels 101 are arrayed. The conversion element 142 for converting the light converted from radiation by the scintillator into an electrical signal is arranged in each pixel 102. A TFT 105 which is a switch element and various kinds of wiring lines are arranged at the lower portion of the conversion element 142. An electrical signal generated by the conversion element 142 by photoelectric conversion is output to the corresponding image signal line 112 via the TFT 105 when the TFT 105 is set to ON by a signal from the corresponding image control wiring line 113. An upper electrode of the conversion element 142 is connected to the power supply wiring line 114 that applies a predetermined voltage. The detection control wiring line 116 passes through the lower portion of the conversion element 142. Although there are pixels 102 through which the detection control wiring line 116 does not pass as shown in FIGS. 2 and 7, FIG. 8A shows the pixel 102 through which the detection control wiring line 116 passes.

FIG. 8B shows the detection pixel 101. The detection pixel 101 can have an arrangement similar to that of the pixel 102, but the signal line for outputting a signal from the conversion element 141 can differ from that of the pixel 102. The lower electrode of the conversion element 141 is connected to the corresponding detection signal line 103 via a TFT 115, and an electrical signal from the conversion element 141 is output to the detection signal line 103 when the TFT 115 is set to ON by the signal from the detection control wiring line 116. A signal accumulated in the conversion element 141 is read out by causing the TFT 115 to perform an ON/OFF operation for the obtainment of the radiation irradiation information such as the measurement of illuminance at radiation irradiation, the detection of the start/end of radiation irradiation, and the like.

Figure 9:
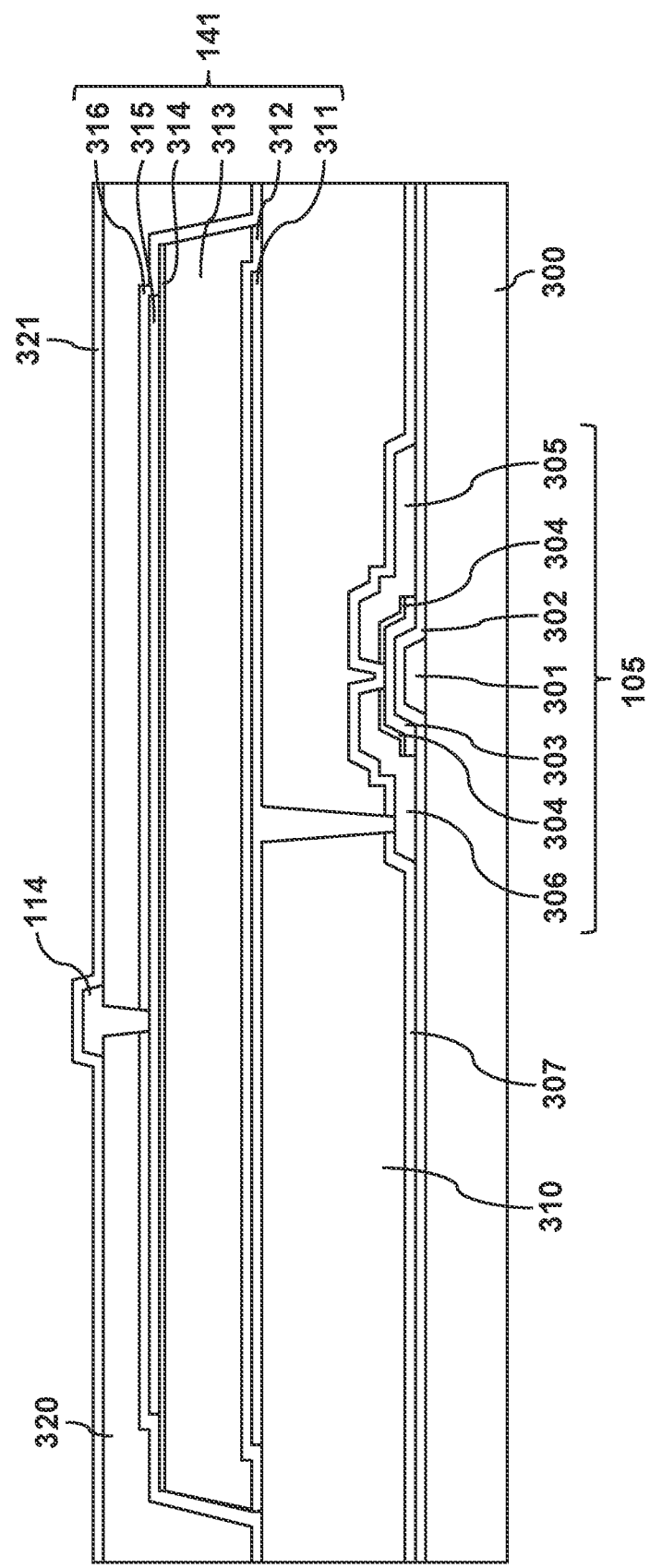
FIG. 9 is a sectional view of the pixel of FIG. 8A.

FIG. 9 shows a sectional view taken along a line A-A' shown in FIG. 8A. The conversion element 142 is arranged above the TFT 105, which is arranged above an insulating substrate 300 such as a glass substrate or the like, with an interlayer insulating layer 310 sandwiched between the conversion element and the TFT. The TFT 105 includes, on the substrate 300, a control electrode 301, an insulating layer 302 which functions as a gate insulating film, a semiconductor layer 303, a heavily doped layer 304 formed by a semiconductor which has an impurity concentration higher than that of the semiconductor layer 303, and main electrodes 305 and 306. A part of the heavily doped layer 304 is in contact with the main electrodes 305 and 306, and a region of the semiconductor layer 303 between the main electrode 305 and the main electrode 306 is the channel region of the TFT 105. The control electrode 301 is electrically connected to the image control wiring line 113, the main electrode 305 is electrically connected to the image signal line 112, and the main electrode 306 is electrically connected to an individual electrode 311 arranged for each conversion element. The main electrodes 305 and 306 and the image signal line 112 are formed by using the same conductive layer when the TFT 105 is to be formed, and the main electrode 305 may form a part of the image signal line 112. An insulating layer 307 and an interlayer insulating layer 310 are arranged above the TFT 105.

The arrangement shown in FIG. 9 illustrates an example that uses, as the TFT 105, an inversely staggered TFT formed by the semiconductor layer 303 which is mainly made of amorphous silicon and the heavily doped layer 304. However, the present invention is not limited to this. For example, a staggered TFT mainly made of polysilicon, an organic TFT, an oxide TFT, or the like may be used as the TFT 105. The interlayer insulating layer 310 covers the TFT 105 and includes a contact hole formed between the main electrode 306 and the individual electrode 311. The individual electrode 311 of the conversion element 141 and the main electrode 306 are electrically connected via the contact hole provided in the interlayer insulating layer 310. On the interlayer insulating layer 310, the conversion element 141 sequentially includes, from the side of the interlayer insulating layer 310, the individual electrode 311, a heavily doped layer 312, a semiconductor layer 313, a heavily doped layer 314, and a common electrode 315 to which a common bias voltage for each pixel is applied from the power supply circuit 150. In this embodiment, the heavily doped layer 312 and the heavily doped layer 314 are semiconductor layers that have different conductivity types from each other, and form a PIN photoelectric conversion element together with the semiconductor layer 313. The photoelectric conversion element is not limited to the PIN photoelectric conversion element and may be, for example, a MIS photoelectric conversion element. An insulating layer 316 is stacked so as to cover the conversion element 141, and an interlayer insulating layer 320 is further stacked on the insulating layer 316. The common electrode 315 of the conversion element 141 is electrically connected to the power supply wiring line 114 arranged on the interlayer insulating layer 320. An insulating layer 321 is arranged as a protective film on the interlayer insulating layer 320 and the power supply wiring line 114. A scintillator (not shown) is stacked on the insulating layer 321 and converts incident radiation into light. The conversion element 141 converts the light that has been generated by the scintillator based on the incident radiation into a signal corresponding to the amount of light. Although this embodiment shows an example in which the radiation is converted into light by the scintillator and the converted light is converted into electrical signals by the conversion elements 141 and 142, a direct conversion element that directly converts incident radiation into an electrical signal may be used. In such a case, an element made of amorphous selenium or the like may be used as the conversion element.

Figure 10:
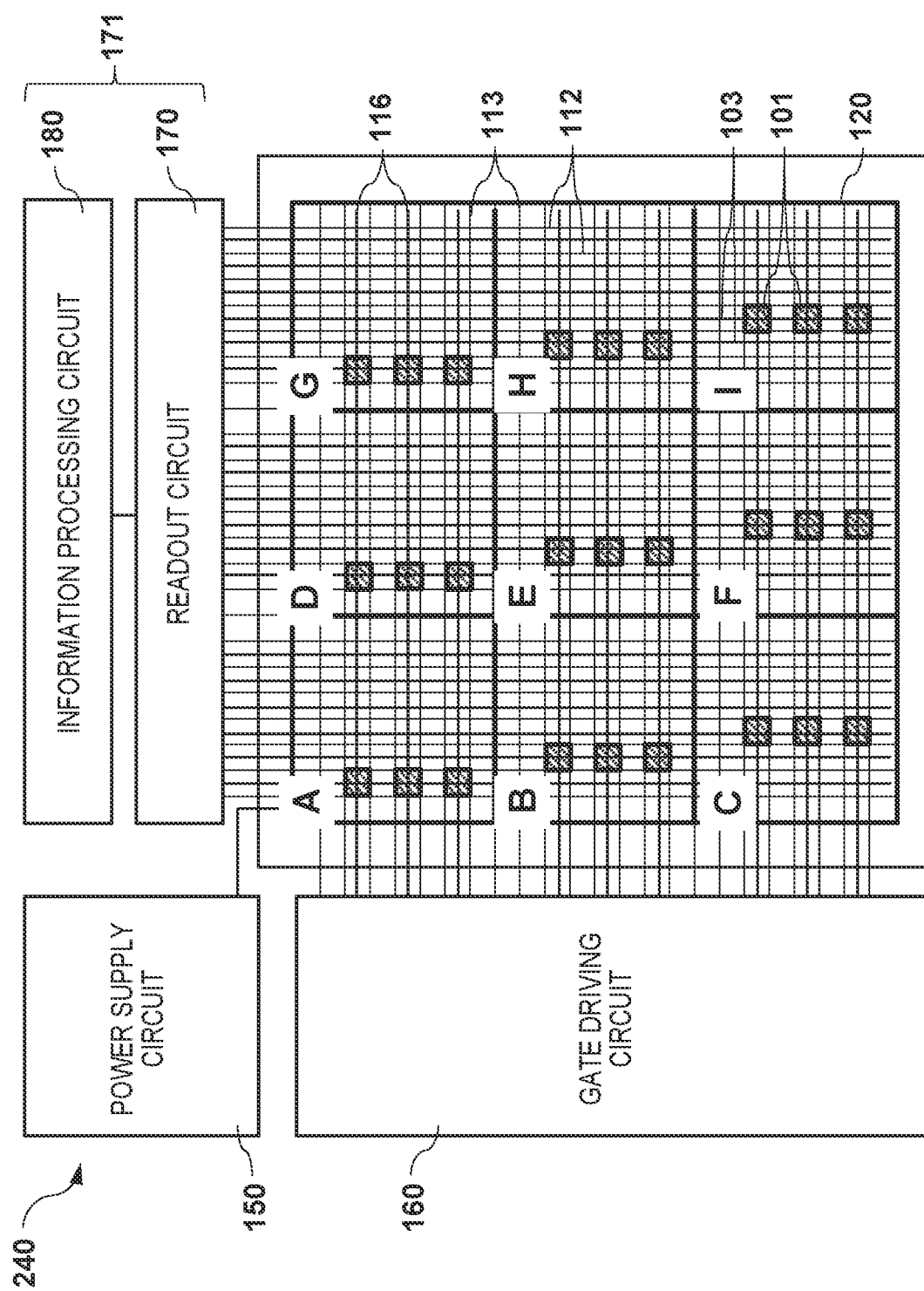
FIG. 10 is a circuit diagram showing an example of the arrangement of the detection pixels of the radiation imaging apparatus of FIG. 1.

FIG. 10 is a circuit diagram showing an example of the arrangement of detection pixels according to this embodiment. The imaging region 120 of the detection unit 240 of the radiation imaging apparatus 100 is divided into nine regions A to I in this embodiment. The division count of the regions is not limited to 9. It may be 8 or less or 10 or more. The detection pixel 101 is arranged in each region, and the dose of the radiation irradiation can be detected for each region. A signal output from the conversion element of each detection pixel 101 is transferred to the information processing circuit 180 via the readout circuit 170 arranged in the peripheral region. This information can be used to use the AEC function for monitoring the dose of incident radiation and stopping the radiation irradiation at the time when the dose reaches an appropriate amount.

In this embodiment, pre-obtained correction data is stored in the storage unit 220, and the control unit 225 uses or processes this correction to determine the correction amount used to perform offset level correction of a signal output from the conversion element of each detection pixel 101. However, the present invention is not limited to this. For example, a signal for determining the correction amount for the accumulation time corresponding to the charge accumulation period may be obtained after the radiation irradiation dose has been confirmed and the signal for generating a radiation image has been obtained.

In this embodiment, the radiation image signal is generated by performing correction in accordance with a correction amount corresponding to a charge accumulation period determined by the control unit 225 for the signal output from the conversion element of each pixel 102. As a result, it is possible to suppress the wait time until signal readout and the degradation of the image quality due to a change in the offset level in an imaging operation without a preset radiation irradiation time.

Figure 11:
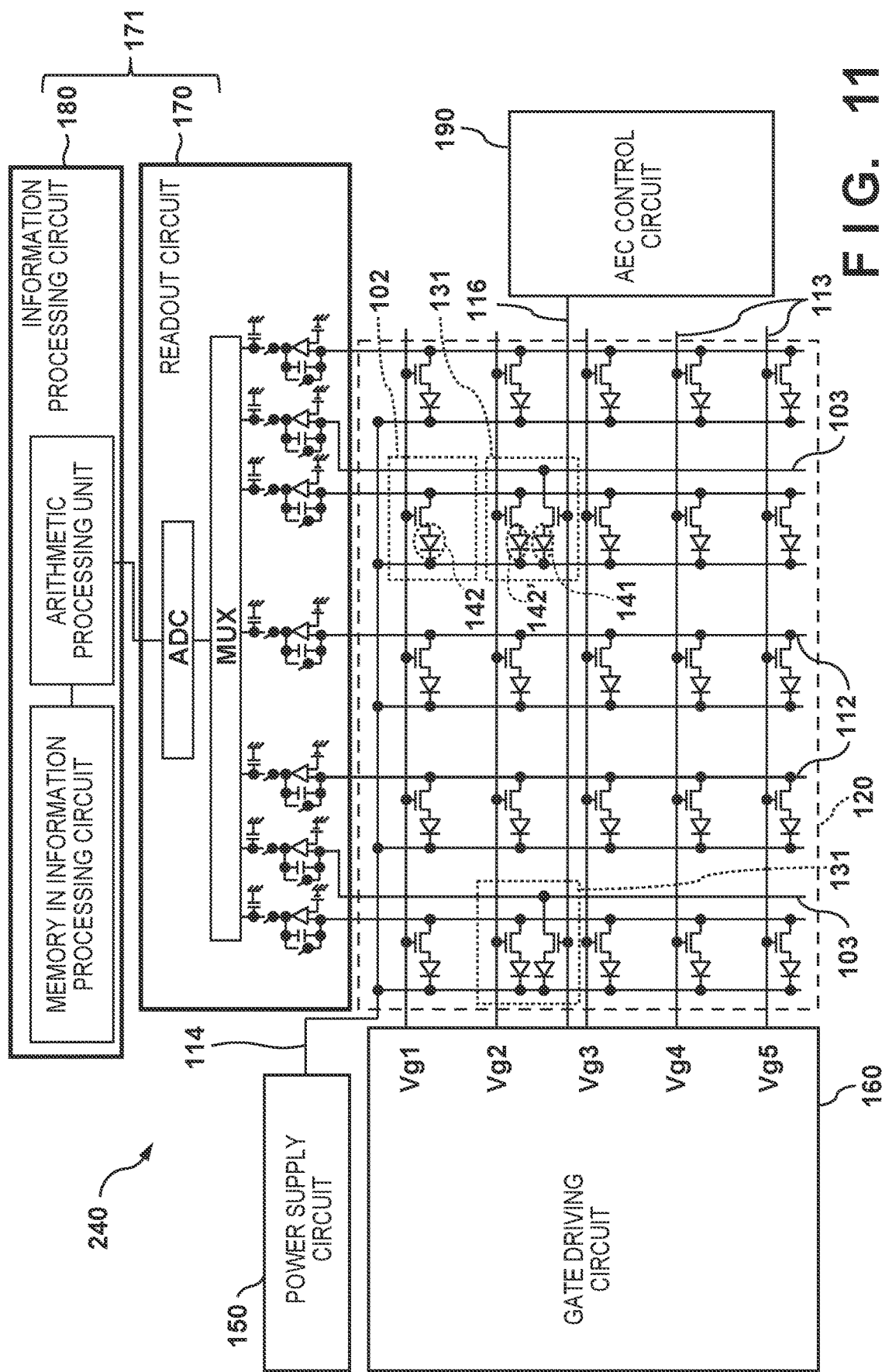
FIG. 11 is a circuit diagram showing a modification of a circuit arrangement of a detection unit of FIG. 2.

An arrangement of a radiation imaging apparatus according to an embodiment of the present invention will be described with reference to FIGS. 11 to 13. FIG. 11 is an equivalent circuit diagram showing an example of the circuit arrangement of a detection unit 240 of a radiation imaging apparatus 100 according to a second embodiment of the present invention. Compared to the detection unit 240 shown in FIG. 7 described above, the arrangement differs in that detection pixels 101 have been changed to detection pixels 131. Each detection pixel 131 includes both a conversion element 142', which is connected to a corresponding image signal line 112 to obtain an image generation signal, and a conversion element 141, which is connected to a corresponding detection signal line 103 to obtain radiation irradiation information. The arrangement of components other than these may be similar to that of the first embodiment described above.

Figure 12:
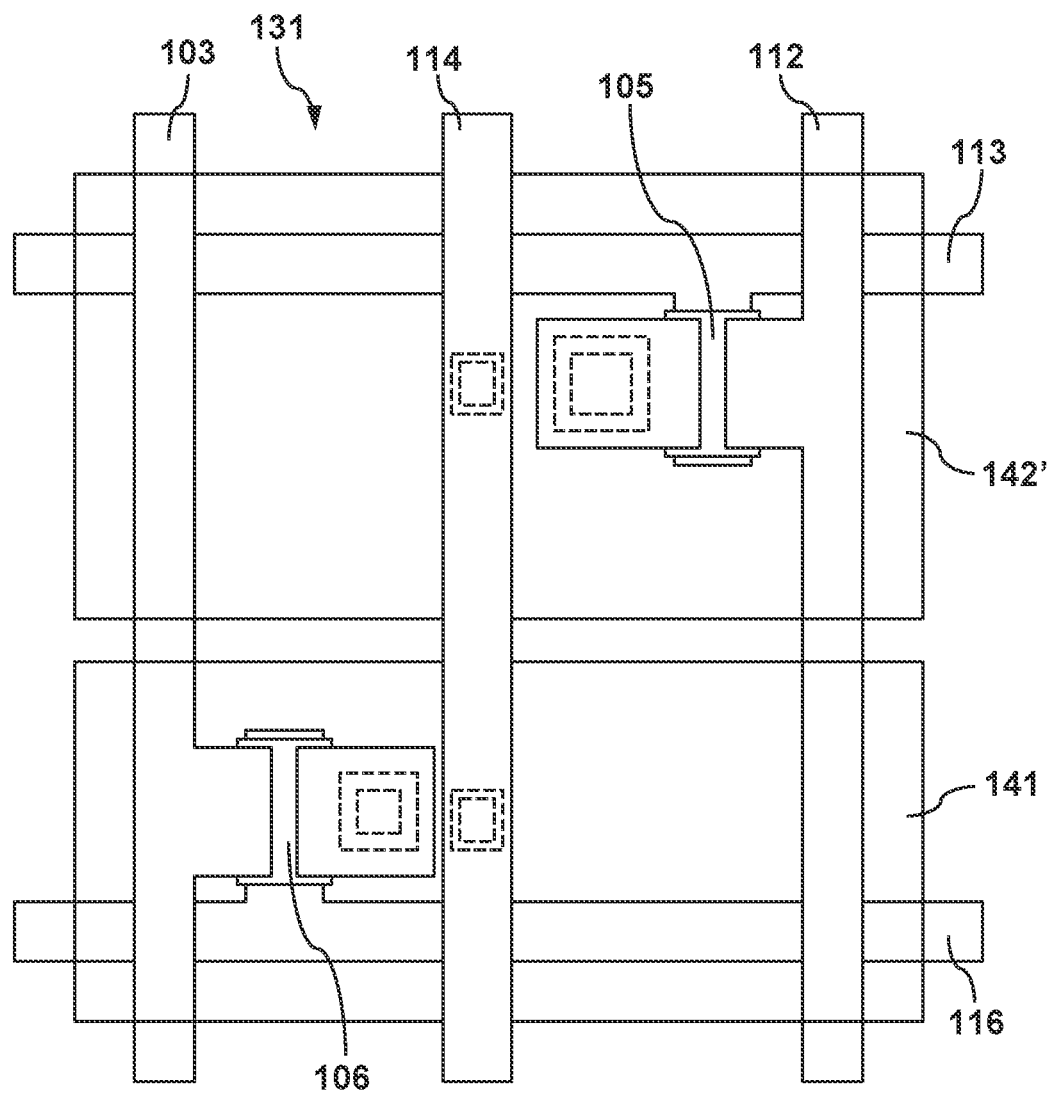
FIG. 12 is a plan view showing a detection pixel of FIG. 11.

FIG. 12 shows a plan view of each detection pixel 131 shown in FIG. 11. The upper side of the detection pixel 131 has an arrangement similar to that of a pixel 102, and includes the conversion element 142' which has a smaller area than a conversion element 142 of the pixel 102. The lower side of the detection pixel 131 has an arrangement similar to that of the detection pixel 101, and includes the conversion element 141 which has a smaller area than the conversion element 142 of the detection pixel 101. Although the area of the conversion element 142' which accumulates charges for generating an image is about ½ the area of the conversion element 142 of the pixel 102, it is possible to obtain an output equal to that of the conversion element 142 of the pixel 102 by executing image processing such as offset correction, gain correction, and the like.

In a case in which dedicated detection pixels 101 are arranged to obtain radiation irradiation information as in the arrangement shown in FIGS. 2 and 7, information for generating a radiation image will be missed because the pixel 102 for image generation cannot be arranged in the position of each detection pixel. To cope with this missing information, the information of the missing portion needs to be corrected by using the signals output from the pixels 102 surrounding the detection pixel 101. The image quality may degrade if there are many such missing information pixels. Hence, by arranging not only the conversion element 141 for obtaining radiation information, but also the conversion element 142' for generating a radiation image in a single pixel, the radiation irradiation information can be obtained without causing image quality degradation.

Figure 13:
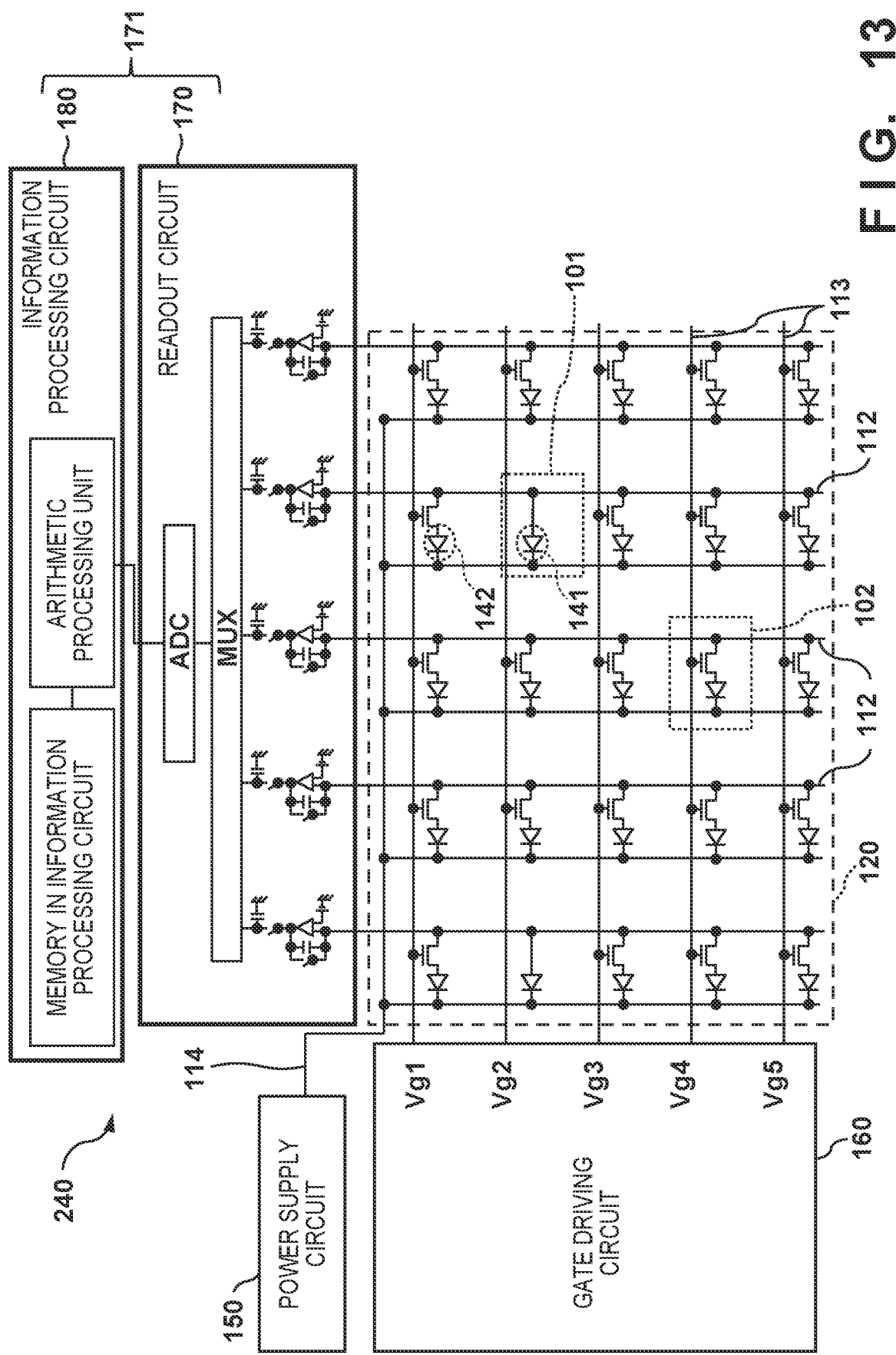
FIG. 13 is a circuit diagram showing a modification of the circuit arrangement of the detection unit of FIG. 2.

FIG. 13 is an equivalent circuit diagram showing the circuit arrangement of the detection unit 240 of the radiation imaging apparatus 100 according to this embodiment, and shows a modification of the circuit arrangement shown in FIGS. 2, 7, and 11. In this embodiment, instead of outputting a signal to the dedicated detection signal line 103, each detection pixel 101 outputs the signal to the image signal line 112 to which a signal is output from the conversion elements 142 of the pixel 102. In addition, the conversion element 141 of the detection pixel 101 is directly connected to the image signal line 112 without the intervention of a switch element using a TFT or the like. In addition, a detection control wiring line 116 for controlling the switch element is not arranged because the switch element is not arranged in the detection pixel 101. Points other than these may have a circuit arrangement similar to those of the equivalent circuit diagrams shown in FIGS. 2, 7, and 11.

In the circuit shown in FIG. 13, the arrangement of a gate driving circuit 160 can be simplified because the conversion element 141 of each detection pixel 101 outputs a signal without the intervention of a switch element. In addition, each image signal line 112 is used for outputting signals from both the conversion element 141 of the detection pixel 101 and the conversion element 142 of the pixel 102. As a result, it is possible to reduce the number of terminals to be connected to a readout circuit 170 and simplify the readout circuit 170.

The embodiments according to the present invention have been described above. However, the present invention is not limited to these embodiments, as a matter of course, and the above-described embodiments can appropriately be changed or combined without departing from the scope of the present invention.

Figure 14A:
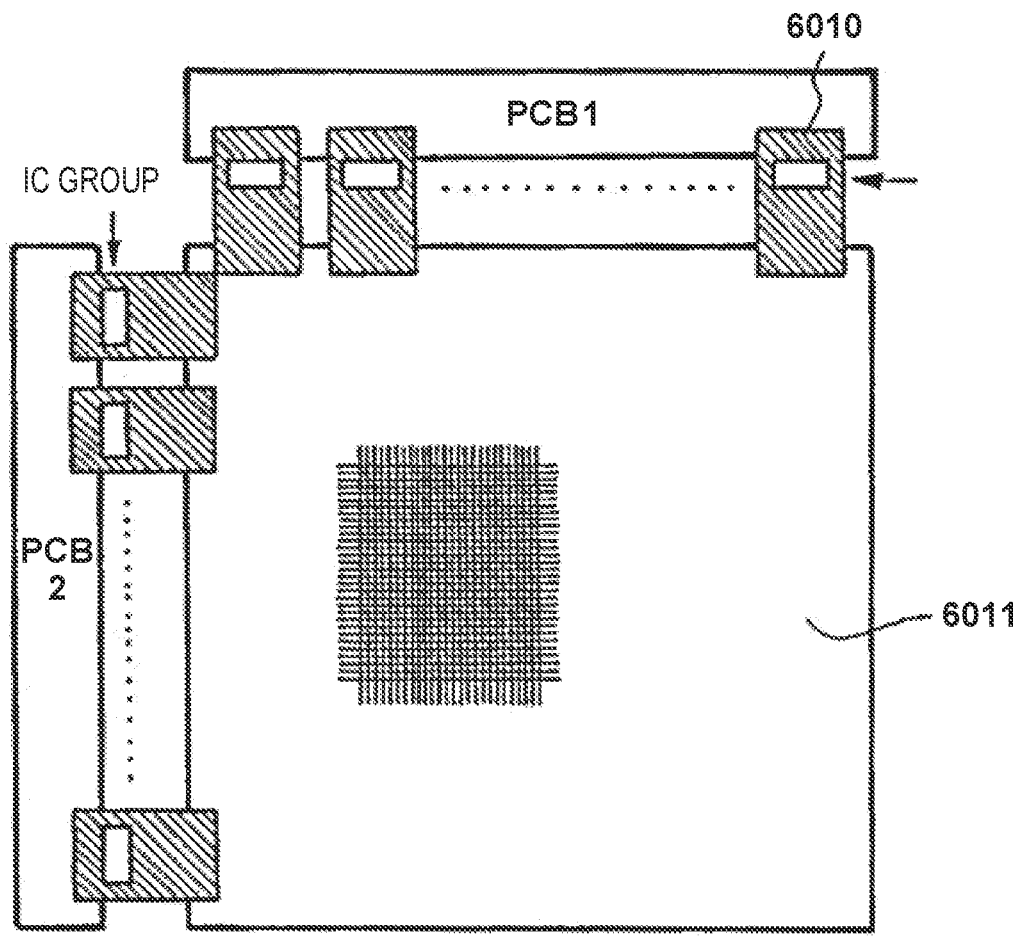
FIG. 14A is a view showing an implementation example of the radiation imaging apparatus of FIG. 1.
Figure 14B:
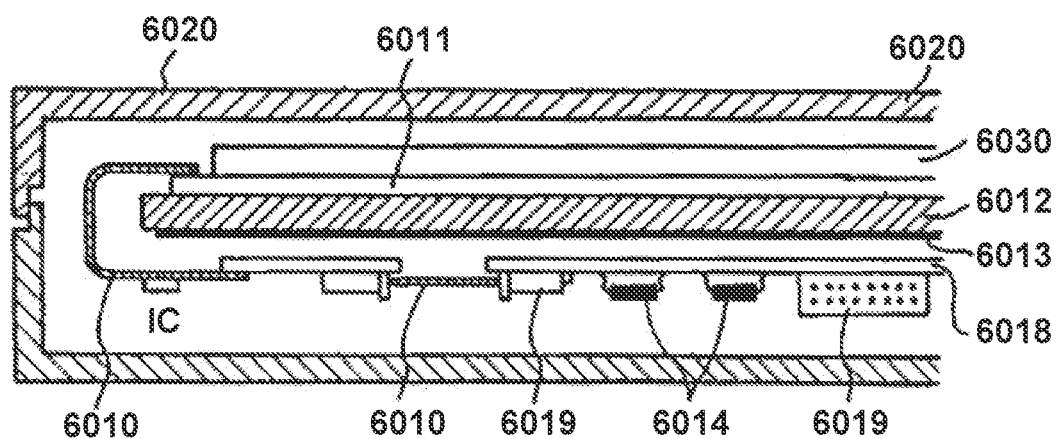
FIG. 14B is a view showing an implementation example of the radiation imaging apparatus of FIG. 1.

An applied embodiment of a radiation imaging apparatus 100 according to the present invention will be described hereinafter with reference to FIGS. 14A, 14B, and 15. FIGS. 14A and 14B are a diagram and a sectional view, respectively, showing an implementation example of the radiation imaging apparatus 100.

Conversion elements 141 and 142 and TFTs 105 and 115 that form detection pixels 101 and pixels 102 are formed in a sensor substrate 6011 and are connected to flexible circuit boards 6010, each of which is mounted with a shift register SR1 and an integrated circuit IC for detection. The opposite side of each flexible circuit board 6010 is connected to a corresponding one of circuit boards PCB1 and PCB2. The sensor substrate 6011 is bonded onto a base 6012, and a lead plate 6013 for protecting memories 6014 in a processing circuit 6018 is arranged below the base 6012 which forms a large photoelectric conversion device. For example, CsI as a scintillator 6030 for converting radiation into visible light has been deposited on the sensor substrate 6011. The entire arrangement is stored in, for example, a carbon fiber case 6020 as shown in FIG. 14B.

Figure 15:
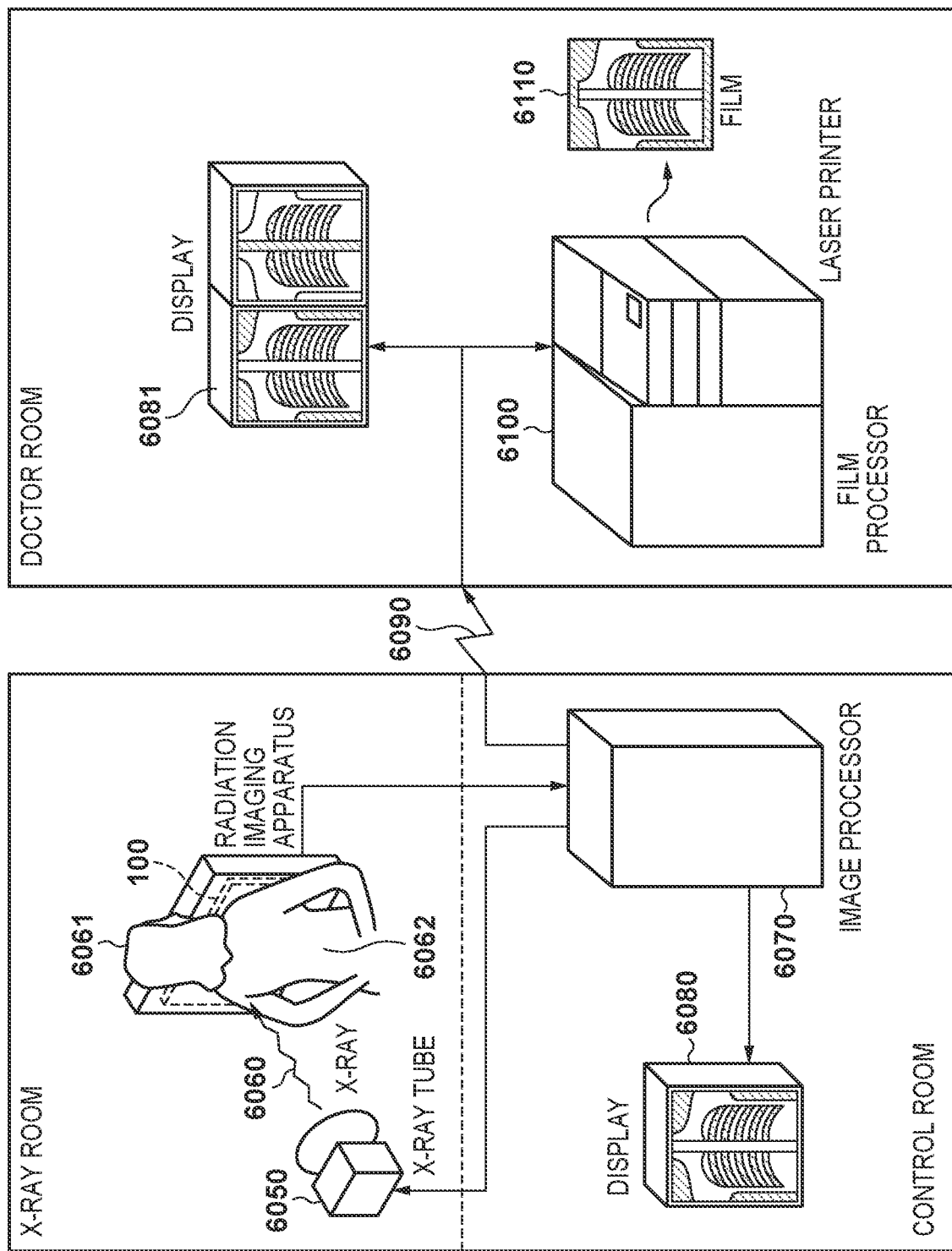
FIG. 15 is a view showing an example of the arrangement of a radiation imaging system using the radiation imaging apparatus of FIG. 2.

A radiation imaging system incorporating the radiation imaging apparatus 100 according to the present invention will be exemplified next with reference to FIG. 15. X-rays 6060 generated by an X-ray tube 6050 serving as a radiation source pass through a chest 6062 of a patient or object 6061 and enter the radiation imaging apparatus 100 according to the present invention. The incident X-rays include information about the internal body of the patient or object 6061. In the radiation imaging apparatus 100, a scintillator emits light in accordance with the entry of the X-rays 6060, and the emitted light is photoelectrically converted by photoelectric conversion elements to obtain electrical information. This information is converted into digital data, undergoes image processing by an image processor 6070 serving as a signal processing unit, and can be observed on a display 6080 serving as a display unit in a control room.

Also, this information can be transferred to a remote place by a transmission processing unit such as a network 6090 which may be, for example, a telephone, a LAN, the Internet, or the like. This allows the information to be displayed on a display 6081 serving as a display unit in a doctor's office or the like in another place and allows even a doctor in a remote place can make a diagnosis. In addition, the information can be saved on a recording medium such as an optical disk, and a film processor 6100 can also record the information on a film 6110 serving as a recording medium.

The solution described above provide a technique advantageous in an imaging operation in which a radiation irradiation time cannot be preset.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging apparatus comprising:
an imaging region in which a plurality of conversion elements are arranged, wherein the plurality of conversion elements includes a first conversion element configured to obtain a radiation image and a second conversion element configured to obtain irradiation information of incident radiation during radiation irradiation;
a storage unit configured to store correction data for correcting a signal output from the first conversion element; and
a control unit,
wherein the control unit
determines a period to cause the first conversion element to perform an accumulation operation in accordance with the irradiation information,
determines a correction amount corresponding to the period based on the correction data, and
generates a radiation image signal by correcting a signal output from the first conversion element in accordance with the correction amount after the radiation irradiation.

2. The radiation imaging apparatus according to claim 1, wherein
the correction data includes a plurality of correction coefficients, and
the control unit selects, as the correction amount, one correction coefficient corresponding to the period from the plurality of correction coefficients.

3. The radiation imaging apparatus according to claim 1, wherein
the correction data includes a plurality of correction coefficients, and
the control unit generates, in accordance with the period, the correction amount from not less than one correction coefficient of the plurality of correction coefficients.

4. The radiation imaging apparatus according to claim 1, wherein
the correction data includes a correction coefficient, and
the control unit generates, in accordance with the period, the correction amount from the correction coefficient.

5. The radiation imaging apparatus according to claim 1, wherein
the irradiation information includes radiation irradiation start information, and
the control unit causes the first conversion element to start the accumulation operation in accordance with the radiation irradiation start information.

6. The radiation imaging apparatus according to claim 5, wherein the control unit obtains the radiation irradiation start information based on a signal output from the second conversion element.

7. The radiation imaging apparatus according to claim 5, wherein the control unit resets the first conversion element before obtaining the radiation irradiation start information.

8. The radiation imaging apparatus according to claim 1, wherein
the irradiation information includes information of a dose of incident radiation based on the signal output from the second conversion element, and
the control unit obtains an accumulated value of the dose, outputs a signal to stop radiation exposure in accordance with the accumulated value reaching a predetermined threshold, and also causes the first conversion element to output a signal.

9. The radiation imaging apparatus according to claim 1, wherein
the irradiation information includes radiation irradiation end information, and
the control unit causes the first conversion element to output the signal in accordance with the radiation irradiation end information.

10. The radiation imaging apparatus according to claim 9, wherein the control unit obtains the radiation irradiation end information based on a signal output from the second conversion element.

11. The radiation imaging apparatus according to claim 5, wherein
the control unit
determines a radiation irradiation time based on the correction data, and
outputs, after obtaining the radiation irradiation start information, a signal to stop radiation exposure in accordance with the radiation irradiation time and also causes the first conversion element to output a signal.

12. A radiation imaging system comprising:
a radiation imaging apparatus according to the claim 1; and
a signal processing unit configured to process a signal from the radiation imaging apparatus.

13. A control method of a radiation imaging apparatus comprising an imaging region in which a plurality of conversion elements are arranged, wherein the plurality of conversion elements includes a first conversion element configured to obtain a radiation image and a second conversion element configured to obtain irradiation information of incident radiation during radiation irradiation, and a storage unit configured to store correction data for correcting a signal output from the first conversion element, the method comprises:
determining a period to cause the first conversion element to perform an accumulation operation in accordance with the irradiation information;
determining a correction amount corresponding to the period based on the correction data; and
generating a radiation image signal by correcting a signal output from the first conversion element in accordance with the correction amount after the radiation irradiation.

14. A non-transitory computer-readable storage medium storing a program for causing a computer to execute a control method for controlling a radiation imaging apparatus comprising an imaging region in which a plurality of conversion elements are arranged, wherein the plurality of conversion elements includes a first conversion element configured to obtain a radiation image and a second conversion element configured to obtain irradiation information of incident radiation during radiation irradiation, and a storage unit configured to store correction data for correcting a signal output from the first conversion element, the method comprises:
- determining a period to cause the first conversion element to perform an accumulation operation in accordance with the irradiation information;
- determining a correction amount corresponding to the period based on the correction data; and
- generating a radiation image signal by correcting a signal output from the first conversion element in accordance with the correction amount after the radiation irradiation.

* * * * *